United States Patent
Su et al.

(10) Patent No.: US 7,361,769 B2
(45) Date of Patent: Apr. 22, 2008

(54) HETEROCYCLYLS AS SELECTIVE MELANIN CONCENTRATING HORMONE RECEPTOR ANTAGONISTS FOR THE TREATMENT OF OBESITY AND RELATED DISORDERS

(75) Inventors: Jing Su, Scotch Plains, NJ (US); Brian A. McKittrick, New Vernon, NJ (US); Haiqun Tang, Belle Mead, NJ (US); Thavalakulamgara K. Sasikumar, Edison, NJ (US); Li Qiang, Edison, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 11/181,255

(22) Filed: Jul. 14, 2005

(65) Prior Publication Data
US 2006/0106031 A1 May 18, 2006

Related U.S. Application Data

(60) Provisional application No. 60/588,492, filed on Jul. 16, 2004.

(51) Int. Cl.
C07D 285/08 (2006.01)
C07D 27/06 (2006.01)
C07D 277/28 (2006.01)
C07D 263/48 (2006.01)
C07D 249/04 (2006.01)
C07D 249/08 (2006.01)
C07D 233/56 (2006.01)
C07D 231/12 (2006.01)
C07D 207/323 (2006.01)
C07D 207/325 (2006.01)

(52) U.S. Cl. ............ 548/128; 548/131; 548/204; 548/236; 548/255; 548/267.6; 548/338.1; 548/375.1; 548/561; 549/76; 549/496

(58) Field of Classification Search ............... 548/205
See application file for complete search history.

(56) References Cited

U.S. PATENT DOCUMENTS

2001/0049373 A1* 12/2001 Chalquest ............... 514/269

OTHER PUBLICATIONS

Sawa, et al.; Recent developments in the design of orally bioavailable beta3-adrenergic receptor agonists. 2006; Current Medicinal Chemistry; 13, 25-37.*
Orbach, S; Drug-drug interactions: an important negative attribute in drugs. 2003, Drugs of Today, 39, 301-338.*

* cited by examiner

Primary Examiner—Kamal A. Saeed
Assistant Examiner—Shawquia Young
(74) Attorney, Agent, or Firm—William Y. Lee; Palaiyur S. Kalyanaraman

(57) ABSTRACT

The present invention discloses compounds of formula I

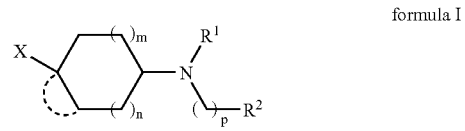

formula I wherein m, n, p, $R^1$, $R^2$ and X, are herein defined, the compounds being novel antagonists for melanin-concentrating hormone (MCH), as well as methods for preparing such compounds. In another embodiment, the invention discloses pharmaceutical compositions comprising such MCH antagonists as well as methods of using them to treat obesity, metabolic disorders, eating disorders such as hyperphagia, and diabetes.

21 Claims, No Drawings

HETEROCYCLYLS AS SELECTIVE MELANIN CONCENTRATING HORMONE RECEPTOR ANTAGONISTS FOR THE TREATMENT OF OBESITY AND RELATED DISORDERS

CROSS REFERENCE TO RELATED APPLICATION

This Application claims the benefit of U.S. Provisional Application No. 60/588,492 filed Jul. 16, 2004.

FIELD OF THE INVENTION

This invention relates to antagonists for melanin-concentrating hormone (MCH) and their use in the treatment of metabolic and eating disorders, novel compounds having MCH receptor modulatory activity, pharmaceutical compositions comprising one or more such modulators, methods of preparing such modulators and methods of using such modulators to treat obesity, diabetes and related disorders.

BACKGROUND OF THE INVENTION

MCH, a cyclic peptide, was first identified over a decade ago in teleost fish where it appears to regulate color change. More recently, MCH has been the subject of investigation for its possible role as a regulator of eating behavior in mammals. As reported by Shimada et al., *Nature*, Vol. 396 (17 Dec. 1998), pp. 670-673, MCH-deficient mice have reduced body weight and leanness due to hypophagia (reduced feeding). In view of their findings, it was suggested that antagonists of MCH may be effective for the treatment of obesity. U.S. Pat. No. 5,908,830 discloses a combination therapy for the treatment of diabetes or obesity involving the administration of a metabolic rate increasing agent and a feeding behavior modifying agent, an example of the latter being an MCH antagonist. Further, MCH receptor antagonists may also be useful in the treatment of depression and/or anxiety. Borowksy et al., *Nature Medicine*, 8, pp. 825-830 (01 Aug. 2002).

WO 03/047568 discloses compounds having MCH antagonistic activity. A desired goal is to find compounds that display low hERG activity to display better and fewer side effects.

SUMMARY OF THE INVENTION

In one embodiment, this invention provides novel heterocyclyl compounds having MCH antagonist activity. These compounds are represented by

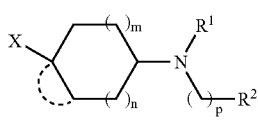

formula I or a pharmaceutically acceptable salt or solvate thereof, wherein

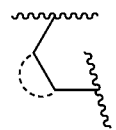

represents either (a) a single bond (b) a double bond, or (c) a cycloalkyl ring where the dashed line is —$(CR^{14}R^{15})_s$—
where s is 1, 2, 3 or 4;
m is 0, 1 or 2;
n is 0 or 1, where the sum of n and m is 1 to 3;
p is 0, 1, 2, 3 or 4;
X is selected from the group consisting of:

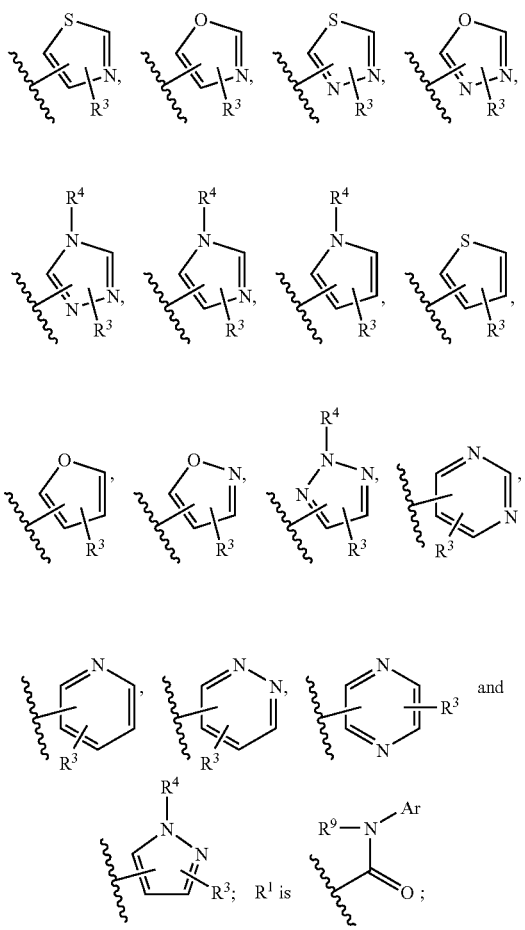

$R^2$ is

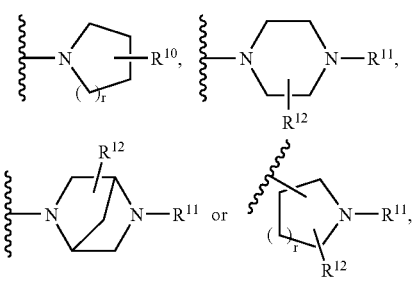

where r is 0, 1, 2 or 3;

$R^3$ is —$(CR^5R^6)_{1-3}$—$NR^7R^8$, or $R^3$ is

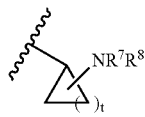

where t is 1, 2, 3, 4 or 5;

$R^4$ is hydrogen or alkyl;

$R^5$ and $R^6$ can be the same or different, each being hydrogen or alkyl;

$R^7$ is hydrogen, alkyl, acyl, alkoxycarbonyl, arylsulfonyl or alkylsulfonyl;

$R^8$ is hydrogen, alkyl, acyl, —$C(O)NH_2$, —$C(O)NH$-alkyl, —$C(O)N(alkyl)_2$, alkoxycarbonyl, arylsulfonyl or alkylsulfonyl;

or $R^7$ and $R^8$, taken together and with the nitrogen to which they are attached, form a heterocyclyl ring, wherein said heterocyclyl ring can be optionally substituted with 1 or 2 ring system substituents, each ring system substituent being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—$NH_2$, —C(=NH)—$NH_2$, —C(=NH)—NH(alkyl), $Y_1Y_2N$—, $Y_1Y_2N$-alkyl-, $Y_1Y_2NC(O)$—, $Y_1Y_2NSO_2$— and —$SO_2NY_1Y_2$, wherein $Y_1$ and $Y_2$ can be the same or different and are independently selected from the group consisting of hydrogen, alkyl, aryl, cycloalkyl, and aralkyl;

$R^9$ is hydrogen or alkyl;

$R^{10}$ is 1 to 3 moieties, each $R^{10}$ is independently selected from the group consisting of hydrogen, hydroxy, alkoxy, alkoxyalkyl, hydroxyalkyl, alkyl and halo, with the proviso that $R^{10}$ cannot be halo when it is attached to the carbon adjacent to N;

$R^{11}$ is hydrogen, alkyl, alkoxyalkyl, hydroxyalkyl, acyl, alkoxycarbonyl, —$C(O)NR^7R^8$, -alkylC(O)$NR^7R^8$, arylsulfonyl, alkylsulfonyl or -alkylC(O)$_2R^4$;

$R^{12}$ is 1 to 4 moieties, each $R^{12}$ is independently selected from the group consisting of hydrogen, alkyl, alkoxyalkyl or hydroxyalkyl;

Ar is $(R^{13})_u$-substituted aryl or $(R^{13})_u$-substituted heteroaryl, where u is a number from 1 to 3; and each $R^{13}$ is independently selected from the group consisting of hydrogen, hydroxy, halo, alkyl, alkoxy, —$OCF_3$, —$CF_3$, —$SO_2$-alkyl, —$NO_2$, —$SCF_3$ and —CN, or two $R^{13}$ moieties on adjacent carbons of the aryl or heteroaryl ring can be linked to form

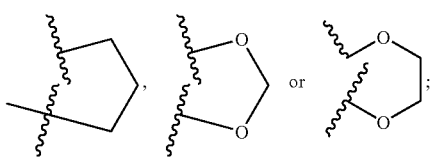

$R^{14}$ is hydrogen, alkyl, —$CH_2OH$, halo, —CN, —OH, alkoxy or —$NR^7R^8$; and $R^{15}$ is hydrogen, alkyl, —$CH_2OH$, halo, —CN, —OH, alkoxy or —$NR^7R^8$.

This invention is also directed to pharmaceutical compositions for the treatment of metabolic disorders such as obesity, those disorders associated with obesity and eating disorders such as hyperphagia, using compounds of formula I or salts or solvates thereof. In one aspect, this invention is directed to the method of treatment of metabolic disorder(s) such as obesity, and/or eating disorder(s) such as hyperphagia using the compound of formula I or salts or solvates thereof. Another embodiment includes a method of treating an eating disorder which comprises administering to a mammal in need of such treatment an amount of a first compound, said first compound being a compound of formula I or salts or solvates thereof; and a second compound, said second compound being an antiobesity and/or anorectic agent wherein the amounts of the first and second compounds result in the desired therapeutic effect. In another aspect, this invention is directed to pharmaceutical compositions for the treatment of obesity which comprise an obesity treating amount of at least one compound of formula 1, or a pharmaceutically acceptable salt or solvate of said compound and a pharmaceutically acceptable carrier.

DETAILED DESCRIPTION

The present invention relates to compounds that are represented by structural formula I, or a pharmaceutically acceptable salt or solvate thereof, wherein the various moieties are as described above.

One aspect of the invention include those compounds of formula I wherein

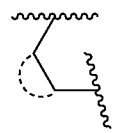

represents either (a) a double bond or (b)

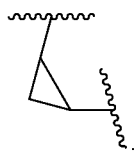

Another aspect of the invention includes those compounds of formula I wherein m is 0 or 1, n is 0 or 1 and p is 2 or 3.

Another aspect of the invention include those compounds of formula I wherein X is selected from the group consisting of:

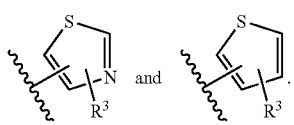

Another aspect of the invention include those compounds of formula I wherein $R^1$ is

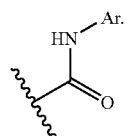

Another aspect of the invention are compounds of formula I wherein $R^2$ is

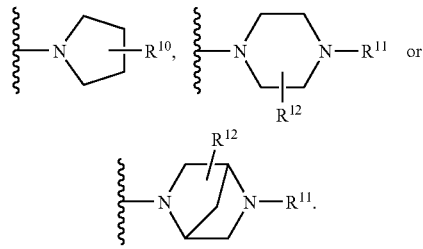

Another aspect of the invention are compounds of formula I wherein $R^3$ is —$CH_2$—$NR^7R^8$, where $R^7$ and $R^8$ can be optionally joined together and with the nitrogen to which they are attached form a heterocyclyl ring, wherein said heterocyclyl ring can be optionally substituted with hydroxy.

Another aspect of the invention are compounds of formula I wherein $R^7$ is hydrogen or alkyl and $R^8$ is hydrogen or alkyl.

Another aspect of the invention are compounds of formula I wherein $R^{10}$ is 1 or 2 moieties and each $R^{10}$ is independently selected from the group consisting of hydrogen, hydroxy and alkoxy.

Another aspect of the invention are compounds of formula I wherein $R^{10}$ is 1 moiety and each $R^{10}$ is independently selected from the group consisting of hydrogen and hydroxy.

Another aspect of the invention are compounds of formula I wherein $R^{11}$ is hydrogen or alkyl.

Another aspect of the invention are compounds of formula I wherein $R^{12}$ is 1 or 2 moieties, where each $R^{12}$ moiety is independently selected from the group consisting of hydrogen, alkyl, hydroxyalkyl and alkoxyalkyl.

Another aspect of the invention are compounds of formula I wherein Ar is $(R^{13})_2$-substituted aryl, $(R^{13})_2$-substituted heteroaryl, wherein each $R^{13}$ is independently selected from the group consisting of halo and —$CF_3$.

Another aspect of the invention are compounds of formula I wherein $R^{14}$ is hydrogen or alkyl and $R^{15}$ is hydrogen or alkyl.

Additional aspects of the invention include those compounds of formula I wherein

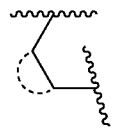

represents either (a) a double bond or (b) —$C(R^{14}R^{15})$—;
m is 1 or 2;
n is 0 or 1;
p is 2 or 3;

X is selected from the group consisting of

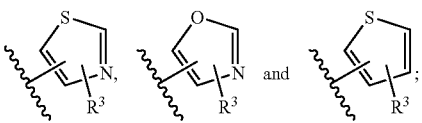

$R^1$ is

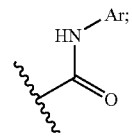

$R^2$ is

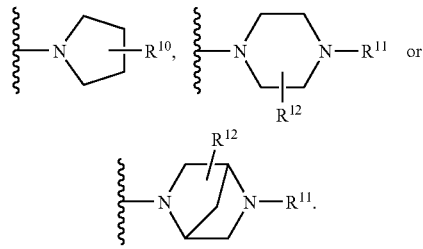

where r is 0, 1, 2 or 3;
$R^3$ is —$C(R^5R^6)$—$NR^7R^8$, or $R^7$ and $R^8$ can be optionally joined together and with the nitrogen to which they are attached, form a heterocyclyl ring, wherein said heterocyclyl ring can be optionally substituted with hydroxy;
$R^7$ is hydrogen or alkyl;
$R^8$ is hydrogen or alkyl;
$R^{10}$ is 1 or 2 moieties and each $R^{10}$ is independently selected from the group consisting of hydrogen, hydroxy and alkoxy;
$R^{11}$ is hydrogen or alkyl;
$R^{12}$ is selected from the group consisting of hydrogen, alkyl, hydroxyalkyl and alkloxyalkyl;
Ar is $(R^{13})_2$-substituted aryl, $(R^{13})_2$-substituted heteroaryl, wherein each $R^{13}$ is independently selected from the group consisting of halo and —$CF_3$;
$R^{14}$ is hydrogen or alkyl; and
$R^{15}$ is hydrogen or alkyl.

Additional aspects of the invention include those compounds of formula I wherein

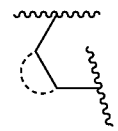

represents either (a) a double bond or (b) —$C(R^{14}R^{15})$—;
m is 1;
n is 0;
p is 2 or 3;

X is selected from the group consisting of

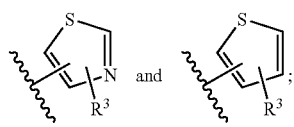

R¹ is

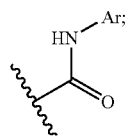

R² is

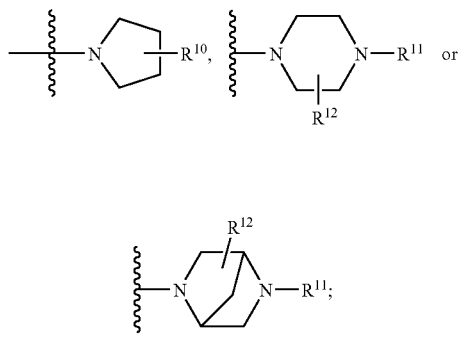

R³ is —C(R⁵R⁶)—NR⁷R⁸, or R⁷ and R⁸ can be optionally joined together and with the nitrogen to which they are attached, form a heterocyclyl ring, wherein said heterocyclyl ring can be optionally substituted with hydroxy;

R⁵ and R⁶ can be the same or different, each being hydrogen or alkyl;

R⁷ is hydrogen or alkyl;

R⁸ is hydrogen or alkyl;

R¹⁰ is hydroxy;

R¹¹ is hydrogen or alkyl;

R¹² is 1 to 4 moieties, each R¹² is independently selected from the group consisting of hydrogen and alkyl;

Ar is (R¹³)$_u$-substituted phenyl, where u is 2; and each R¹³ is independently selected from the group consisting of hydrogen, halo, —OCF₃, —CF₃ and —CN;

R¹⁴ is hydrogen or alkyl; and

R¹⁵ is hydrogen or alkyl.

Preferred embodiments of formula I include compounds selected from the group consisting of Examples 1-21.

Additional preferred embodiments of formula I include compounds of the following formulae:

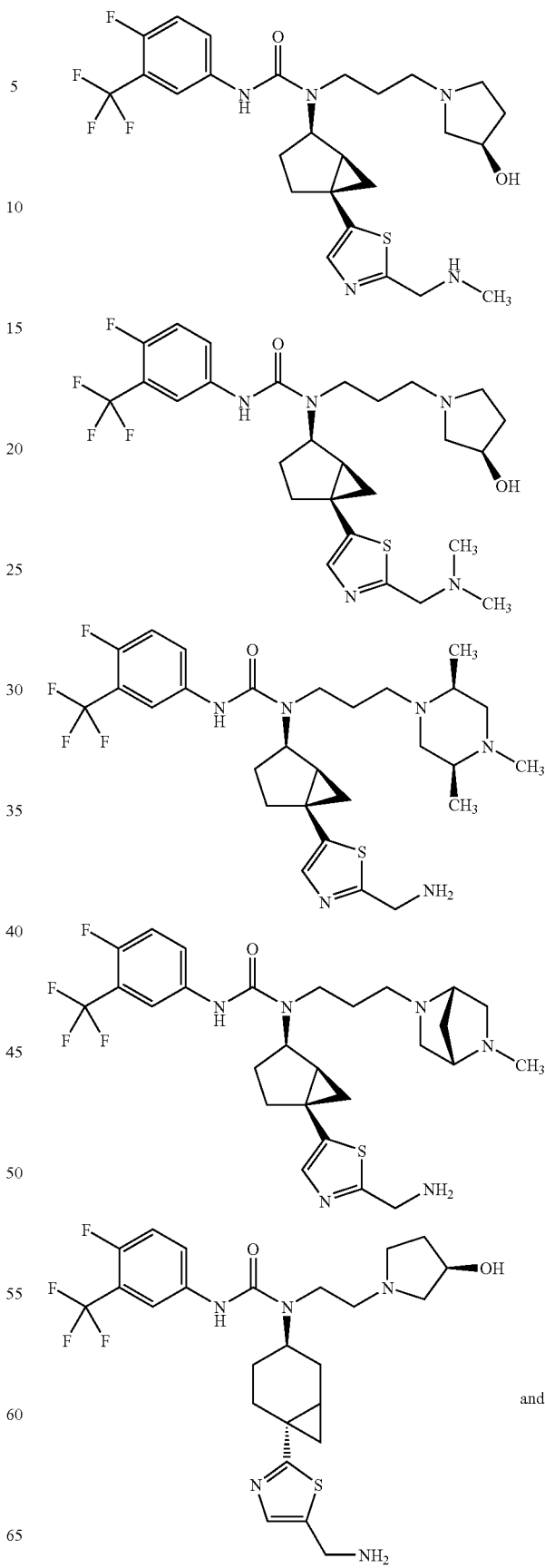

-continued

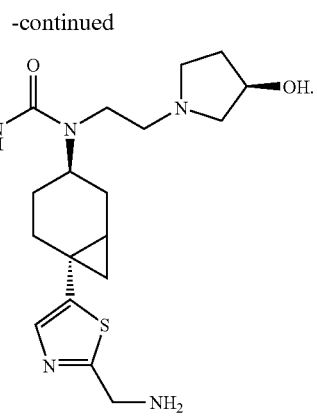

Except where stated otherwise, the following definitions apply throughout the present specification and claims. These definitions apply regardless of whether a term is used by itself or in combination with other terms. Hence the definition of "alkyl" applies to "alkyl" as well as to the "alkyl" portions of "alkoxy", "cycloalkyl" and so forth.

As used above, and throughout the specification, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. The term "substituted alkenyl" means that the alkenyl group may be substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Halogen" means fluorine, chlorine, bromine, or iodine. Preferred are fluorine, chlorine and bromine.

"Halo" means fluoro, chloro, bromo or iodo. Preferred are fluoro, chloro and bromo.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

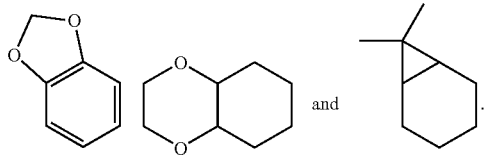

"Heterocyclyl" means a non-aromatic saturated monocyclic or multicyclic ring system comprising about 3 to about 10 ring atoms, preferably about 4 to about 7 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

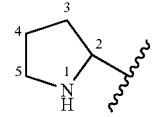

there is no —OH attached directly to carbons marked 2 and 5.

It should also be noted that tautomeric forms such as, for example, the moieties:

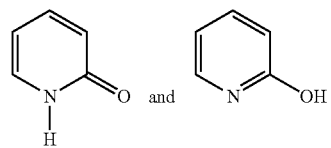

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Heteroaralkylthio" means a heteroaralkyl-S— group in which the heteroaralkyl is as previously described. Preferred heteroaralkylthios contain a lower alkyl group. The bond to the parent moiety is through the sulfur.

"Heteroarylalkenyl" means a heteroaryl-alkenyl group in which the heteroaryl and the alkenyl are as previously described. Preferred heteroarylalkenyls contain a lower alkenyl group. The bond to the parent moiety is through the alkyl.

"Heteroarylalkynyl" means a heteroaryl-alkynyl group in which the heteroaryl and the alkynyl are as previously described. Preferred heteroarylalkynyls contain a lower alkynyl group. The bond to the parent moiety is through the alkynyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Alkoxyalkyl" means an alkoxy-alkyl group in which the alkoxy and alkyl groups are as previously described. Non-limiting examples of suitable alkoxyalkyl groups include methoxymethyl and ethoxymethyl. The bond to the parent moiety is through the alkyl group.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylheteroaryl" means an alkyl-heteroaryl group in which the alkyl and heteroaryl groups are as previously described. The bond to the parent moiety is through the heteroaryl.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—C(O)— group in which the alkyl group is as previously described. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group in which the aryl group is as previously described. Non-limiting examples of suitable aryloxycarbonyl groups include phenoxycarbonyl and naphthoxycarbonyl. The bond to the parent moiety is through the carbonyl.

"Aralkoxy" means an aralkyl-O— group in which the aralkyl group is as previously described. A non-limiting example of a suitable aralkoxy is benzyloxy. The bond to the parent moiety is through the oxygen.

"Aralkoxycarbonyl" means an aralkyl-O—C(O)— group in which the aralkyl group is as previously described. Non-limiting example of a suitable aralkoxycarbonyl group is benzyloxycarbonyl. The bond to the parent moiety is through the carbonyl.

"Alkylsulfonyl" means an alkyl-S($O_2$)— group in which the alkyl group is as previously described. Preferred groups are those in which the alkyl group is lower alkyl. The bond to the parent moiety is through the sulfonyl.

"Arylsulfonyl" means an aryl-S($O_2$)— group in which the aryl group is as previously described. The bond to the parent moiety is through the sulfonyl.

"Heteroarylsulfonyl" means a heteroaryl-S($O_2$)— group in which the heteroaryl group is as previously described. The bond to the parent moiety is through the sulfonyl.

"Heteroarylthio" means a heteroaryl-S— group in which the heteroaryl group is as previously described. The bond to the parent moiety is through the sulfur.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any heteroatom with unsatisfied valences in the text, schemes, examples and Tables herein is assumed to have the hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula I or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula I, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

Compounds of Formula I can be highly selective, high affinity Melanin Concentrating Hormone (MCH) receptor antagonists useful for the treatment of obesity.

An aspect of this invention is a method of treating a mammal (e.g., human) having a disease or condition mediated by MCH by administering a therapeutically effective amount of at least one compound of Formula I, or a pharmaceutically acceptable salt or solvate of said compound to the mammal.

"Effective amount" or "therapeutically effective amount" is meant to describe an amount of compound of the present invention effective to treat a mammal (e.g., human) having a disease or condition mediated by MCH, and thus producing the desired therapeutic effect, for example weight loss, diabetes control.

A preferred dosage is about 0.001 to 1000 mg/kg of body weight/day of the compound of Formula I or a pharmaceutically acceptable salt or solvate thereof. An especially preferred dosage is about 0.01 to 30 mg/kg of body weight/day of a compound of Formula I, or a pharmaceutically acceptable salt or solvate of said compound.

Still yet another aspect of this invention is a method of treating obesity comprising administering to a mammal in need of such treatment a therapeutically effective amount of at least one compound of Formula I, or a pharmaceutically acceptable salt or solvate of said compound.

A further aspect of this invention is a method for treating eating and metabolic disorders such as bulimia and anorexia comprising administering to a mammal a therapeutically effective amount of at least one compound of Formula I, or a pharmaceutically acceptable salt or solvate of said compound.

Another aspect of this invention is a method for treating hyperlipidemia comprising administering to a mammal a therapeutically effective amount of at least one compound of Formula I or a pharmaceutically acceptable salt or solvate of said compound.

Another aspect of this invention is a method for treating cellulite and fat accumulation comprising administering to a mammal a therapeutically effective amount of at least one compound of Formula I, or a pharmaceutically acceptable salt or solvate of said compound.

Another aspect of this invention is directed to a method for treating type II diabetes comprising administering to a mammal a therapeutically effective amount of at least one compound of Formula I or a pharmaceutically acceptable salt or solvate of said compound.

In addition to the "direct" effect of the compounds of this invention on the MCH subtype, there are diseases and conditions that can benefit from the weight loss such as, for example, insulin resistance, impaired glucose tolerance, Type II Diabetes, hypertension, hyperlipidemia, cardiovascular disease, gall stones, certain cancers, and sleep apnea.

This invention is also directed to pharmaceutical compositions, which comprise at least one compound of Formula I, or a pharmaceutically acceptable salt or solvate of said compound and at least one pharmaceutically acceptable carrier.

This invention is also directed to pharmaceutical compositions for the treatment of obesity which comprise an obesity treating amount of at least one compound of Formula I, or a pharmaceutically acceptable salt or solvate of said compound and at least one pharmaceutically acceptable carrier.

Still yet other aspects of this invention are combinations of a compound of Formula I, or a pharmaceutically acceptable salt or solvate of said compound and other compounds as described below.

Accordingly, included within the invention is a method for treating obesity comprising administering to a mammal (e.g., a female or male human)
a. an amount of a first compound, said first compound being a compound of Formula I, or a pharmaceutically acceptable salt or solvate of said compound; and
b. an amount of a second compound, said second compound being an antiobesity and/or anorectic agent such as a $\beta_3$ agonist, a thyromimetic agent, an anoretic agent, or an NPY antagonist and/or optionally a pharmaceutically carrier, vehicle or diluent, wherein the amounts of the first and second compounds result in a therapeutic effect (treating obesity).

Another aspect of this invention is a kit comprising:
a. an amount of a compound of Formula I, or a pharmaceutically acceptable salt or solvate of said compound and a pharmaceutically acceptable carrier, vehicle or diluent in a first unit dosage form;
b. an amount of an antiobesity and/or anorectic agent such as a $\beta_3$ agonist, a thyromimetic agent, an anoretic agent, or an NPY antagonist and a pharmaceutically acceptable carrier, vehicle or diluent in a second unit dosage form; and
c. means for containing said first and second dosage forms wherein the amounts of the first and second compounds result in a therapeutic effect.

Preferred antiobesity and/or anorectic agents (taken singly or in any combination thereof) in the above combination methods, combination compositions and combination kits are:

phenylpropanolamine, ephedrine, pseudoephedrine, phentermine, a cholecystokinin-A (hereinafter referred to as CCK-A) agonist, a monoamine reuptake inhibitor (such as sibutramine), a sympathomimetic agent, a serotonergic agent (such as dexfenfluramine or fenfluramine), a dopamine agonist (such as bromocriptine), a melanocyte-stimulating hormone receptor agonist or mimetic, a melanocyte-stimulating hormone analog, a cannabinoid receptor antagonist, a melanin concentrating hormone antagonist, the OB protein (hereinafter referred to as "leptin"), a leptin analog, a leptin receptor agonist, a galanin antagonist or a GI lipase inhibitor or decreaser (such as orlistat). Other useful anorectic agents include bombesin agonists, dehydroepiandrosterone or analogs thereof, glucocorticoid receptor agonists and antagonists, orexin receptor antagonists, urocortin binding protein antagonists, agonists of the glucagon-like peptide-1 receptor such as Exendin and ciliary neurotrophic factors such as Axokine.

Another aspect of this invention is a method of treating diabetes comprising administering to a mammal (e.g., a female or male human)
a. an amount of a first compound, said first compound being a compound of Formula I, or a pharmaceutically acceptable salt or solvate of said compound; and
b. an amount of a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone or GW-1929, a sulfonylurea, glipazide, glyburide, or chlorpropamide wherein the amounts of the first and second compounds result in a therapeutic effect.

This invention is also directed to a pharmaceutical combination composition comprising: a therapeutically effective amount of a composition comprising
a first compound, said first compound being a compound of Formula I, or a pharmaceutically acceptable salt or solvate of said compound;
a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide; and optionally a pharmaceutical carrier, vehicle or diluent.

Another aspect of this invention is a kit comprising:
a. an amount of a compound of Formula I, or a pharmaceutically acceptable salt or solvate of said compound and a pharmaceutically acceptable carrier, vehicle or diluent in a first unit dosage form;
b. an amount of an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide and a pharmaceutically acceptable carrier, vehicle or diluent in a second unit dosage form; and
c. means for containing said first and second dosage forms wherein the amounts of the first and second compounds result in a therapeutic effect.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 1000 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 50 mg/day, in two to four divided doses.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

Compounds of Formula I can be produced by processes known to those skilled in the art using either solution phase or solid phase synthesis as shown in the following reaction schemes, in the preparations and examples below.

Synthesis

The invention disclosed herein is exemplified by the following preparations and examples which should not be construed to limit the scope of the invention which is defined in the appended claims. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% CH$_3$CN, 5 min—95% CH$_3$CN, 7 min—95% CH$_3$CN, 7.5 min—10% CH$_3$CN, 9 min—stop. The observed parent ion using electro spray ionization are given.

The following abbreviations are utilized throughout the experimental procedures described below:
OTf means trifuoromethane sulfonate;
TBDPSCI means tert-butyldiphenylsilyl chloride;
TBAF means tetrabutylammonium fluoride;
Ti(OiPr)$_4$ means titanium isopropoxide;
DPPA means diphenylphosphoryl azide;
DBU means 1,8 diazabicyclo[5.4.0]undec-7-ene;
Ph$_3$P means triphenyl phosphine;
Bn means benzyl;
Me means methyl;
THF means tetrahydrofuran;
DCM means dichloromethane;
Boc means Butoxycarbonyl;
NMR means nuclear magnetic resonance spectroscopy;
MS means mass spectrometry;
room temperature or rt (ambient) means about 25° C.

Alternative mechanistic pathways and analogous structures within the scope of the invention would be apparent to those skilled in the art.

EXPERIMENTAL EXAMPLES

The following examples illustrate the preparation of some of the compounds of the invention and are not to be construed as limiting the scope of the invention disclosed herein.

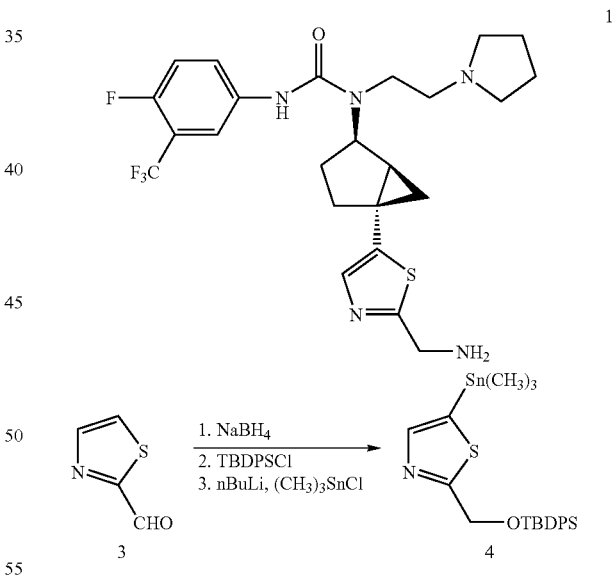

Aldehyde 3 (5.8 g, 51.3 mmol, 1 eq)/10 mL methanol was treated with NaBH$_4$ (2.1 g, 1.1 eq) at 0° C. for 3 h. The solvent was removed and EtOAc was added for extraction. Flash chromatography (2:1 Hexane:EtOAc) provided 3.4 g of the desired product (58% yield).

$^1$H NMR (CDCl$_3$ δ): 4.90 (s, 2H) 7.27 (m, 1H) 7.70 (m, 1H)

This material (3.4 g, 29.6 mmol, 1 eq) was treated with TBDPSCI (8.94 g, 1.1 eq), imidazole (4.0 g, 2 eq) in 20 mL DCM. The mixture was stirred for 14 h. After removal of solvent, extraction with EtOAc and drying the organic layer with Na$_2$CO$_3$, evaporation of the solvent afforded 10.5 g of the desired product quantitavely.

$^1$H NMR (CDCl$_3$ δ): 1.1 (s, 9H) 4.90 (s, 2H) 7.30-7.40 (m, 7H) 7.60-7.70 (m, 5 H)

The thiazole (9.6 g, 27.1 mmol, 1 eq) was dissolved in 100 mL anhydrous THF at −78° C. under nitrogen and treated with 18.6 mL nBuLi (1.6 M in hexane, 1.1 eq). After 5 min, 30 mL trimethyltin chloride (1 M in THF, 1.1 eq) was added in. After 40 min, the reaction was quenched by brine solution. Removal of THF, extraction with 5% EtOAc in hexane and flash chromatography (95:5 Hexane:EtOAc) provided 11.5 g of a mixture (starting material:product 4=1:5, 73% yield).

$^1$H NMR (CDCl$_3$ δ): 1.00 (s, 9 H) 1.1 (s, 9 H) 4.96 (s, 2H) 7.30-7.40 (m, 6 H) 7.60-7.70 (m, 5 H)

For the Synthesis of [3,1,0]bicyclohexyl Analogs (Method 1):

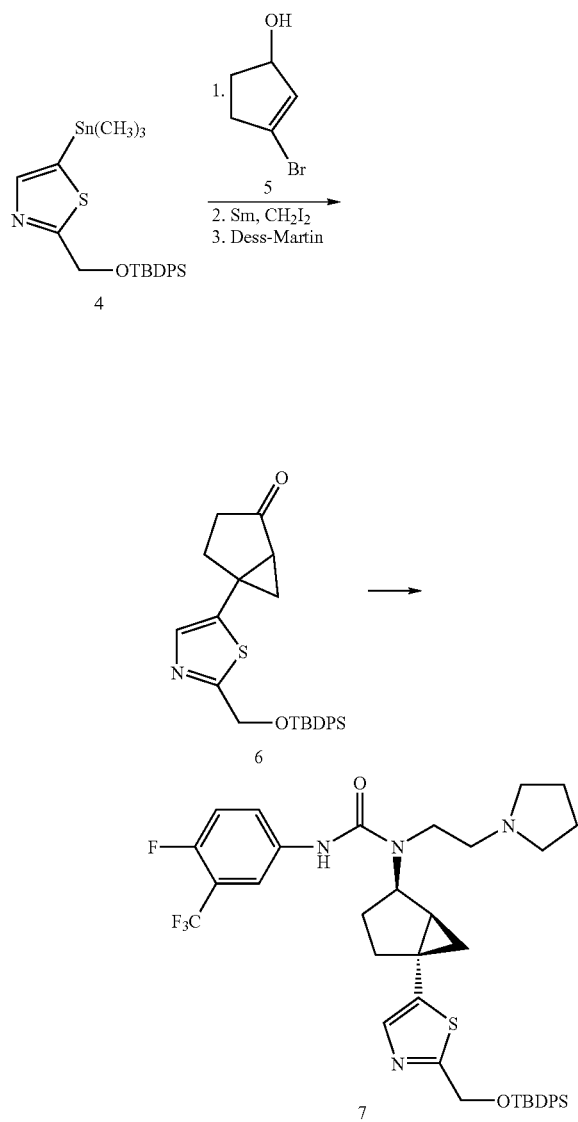

Compound 4 (10.53 g, 16.9 mmol, 1.2 eq) was mixed with 3-bromo-2-cyclopenten-1-ol 5 (2.3 g, 1 eq), tetrakis(triphenylphosphine)palladium (1.63 g, 0.1 eq), LiCl (1.8 g, 3 eq), Na$_2$CO$_3$ (4.5 g, 3 eq) in 100 mL THF at 70° C. under nitrogen for overnight. After removal of solvent, extraction with EtOAc, flash chromatography (3:1 to 2:1 Hexane:EtOAc) provided 3.8 g of the desired product (62% yield).

$^1$H NMR (CDCl$_3$ δ): 1.10 (s, 9 H) 1.80-1.95 (m, 2 H) 2.40 (m, 1H) 2.60 (m, 1 H) 2.80 (m, 1H) 4.86 (s, 2H) 4.90 (m, 1H) 6.00 (s, 1H) 7.30-7.40 (m, 6H) 7.44 (s, 1H) 7.60 (d, 4H, J=6.1 Hz)

HRMS for (MH$^+$) C$_{25}$H$_{30}$NO$_2$SSi: calcd: 436.1722; found: 436.1767.

For the cyclopropanation reaction, 0.52 g samarium (Aldrich, 3.44 mmol, 5 eq) was flame dried under vacuum and cooled with argon. Then it was treated with 4 mL anhydrous THF and cooled to −50° C. under argon. 0.28 mL diiodomethane (5 eq) was added and the mixture was warmed up to −25° C. when the color turned dark green. The olefin (0.3 g, 1 eq) in 3 mL THF was transferred into the green solution and the reaction was followed by TLC. After one hour (temperature at 5° C.), the TLC showed disappearance of the olefin and the reaction was quenched by saturated Na$_2$CO$_3$. Extraction with EtOAc three times. Flash chromatography (2:1 Hexane:EtOAc) provided 0.16 g of the desired product (52% yield).

$^1$H NMR (CDCl3 δ major isomer): 0.80 (m, 1H) 1.00 (m, 1H) 1.10 (s, 9H) 1.30 (m, 1 H) 1.60 (br s, 1 H) 1.80 (m, 1 H) 2.05-2.18 (m, 2 H) 2.40 (m, 1 H) 4.66 (br s, 1 H) 4.82 (s, 2 H) 7.30-7.40 (m, 7 H) 7.60 (d, 4 H, J=6.5 Hz)

The alcohol (1.14 g, 2.54 mmol, 1 eq) was treated with Dess-Martin reagent (1.18 g, 1.1 eq) in 15 mL DCM for overnight. The solvent was removed and extraction with 1:1 EtOAc and hexane followed by washing with saturated Na$_2$CO$_3$. Flash chromatography (2:1 Hexane:EtOAc) provided 1.08 g of the desired product 6 (95% yield).

$^1$H NMR (CDCl$_3$ δ): 1.05 (s, 9 H) 1.20 (m, 1 H) 1.66 (m, 1 H) 2.10 (m, 1 H) 2.20 (m, 2 H) 2.30-2.50 (m, 2 H) 4.85 (s, 2 H) 7.30-7.40 (m, 7 H) 7.60 (d, 4 H, J=6.5 Hz) HRMS for (MH$^+$) C$_{26}$H$_{29}$NO$_2$SSi: calcd: 447.1767; found: 447.1763.

Molecular sieve 3 Å (3.8 g) was flame dried under vacuum. After cooling, the ketone 6 (0.47 g, 1.06 mmol, 1 eq) was mixed with N-(2-aminoethyl)pyrrolidine (0.14 g, 1.1 eq) and stirred overnight. The mixture was treated with 0.071 g of NaBH$_4$ and 5 mL of methanol. After 30 min, the mixture was filtered and flash chromatography (8:1:92 MeOH:NH$_3$:DCM) provided 0.57 g of the desired product.

$^1$H NMR (CDCl$_3$ δ): 0.90 (m, 1 H) 1.05 (s, 9 H) 1.15 (m, 1 H) 1.60-1.90 (m, 4 H) 2.00-2.15 (m, 5 H) 2.70 (m, 2 H) 2.90 (m, 2 H) 3.02 (m, 1 H) 3.10-3.25 (m, 3 H) 3.58 (m, 1 H) 4.80 (s, 2 H) 7.34-7.40 (m, 7 H) 7.60 (d, 4 H, J=6.3 Hz)

$^{13}$C NMR (CDCl$_3$ δ): 14.7 19.7 23.9 26.3 27.2 28.7 32.3 32.5 47.6 54.6 56.5 60.2 64.5 128.3 130.4 133.1 135.9 137.9 144.8 170.1 HRMS for (MH$^+$) C$_{32}$H$_{44}$N$_3$OSSi: calcd: 546.2774; found: 546.2778.

The amine intermediate was treated with 0.24 g of 4-fluoro-3-trifluoromethylphenyl isocyanate (1.2 eq) in 8 mL DCM. After 2 h, 0.2 g of resin bound trisamine was added and after 1 h, filtration through celite gave 0.64 g of the desired product 7. MS for (MH+) $C_{40}H_{46}F_4N_4O_2SSi$: 751.

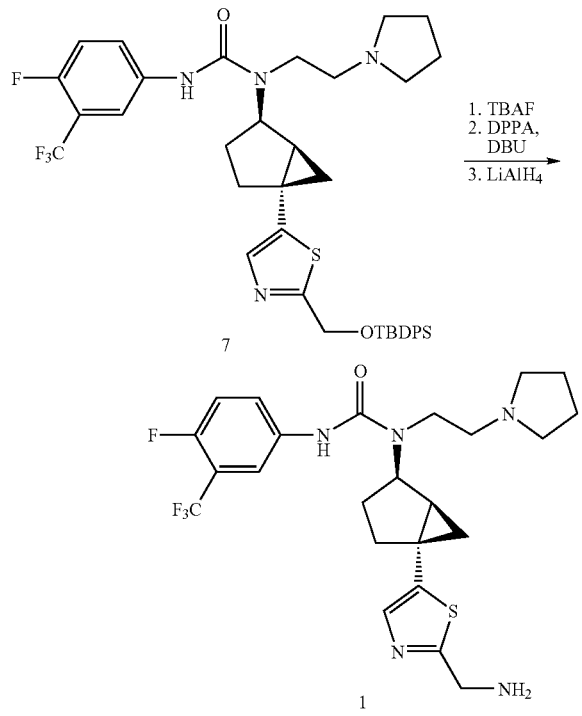

The above urea, compound 7, (0.64 g) was treated with 1.2 mL TBAF (1 M in THF) in 10 mL DCM for 3 h. After removal of solvent, flash chromatography (5:1:95 MeOH:NH$_3$:DCM) provided 0.33 g of the desired alcohol (66% yield in three steps).

$^1$H NMR (CDCl$_3$ δ): 1.00 (m, 1 H) 1.20 (m, 2 H) 1.56 (m, 1 H) 1.80-2.10 (m, 8 H) 2.60-2.90 (m, 6 H) 3.20-3.50 (m, 2 H) 4.78 (s, 2 H) 5.00 (m, 1 H) 7.00 (m, 1 H) 7.30 (s, 1 H) 7.34-7.40 (m, 1 H) 7.58 (m, 1 H) 11.2 (s, 1 H, N—H)

$^{13}$C NMR (CDCl$_3$ δ): 15.9 23.7 24.2 30.2 31.4 42.8 53.9 55.1 59.7 62.3 117.4 117.6 124.4 137.7 138.2 144.6 154.6 155.4 158.1 170.0 HRMS for (MH+) $C_{24}H_{29}F_4N_4O_2S$: calcd: 513.1947; found: 513.1954.

The above product was treated with DBU (0.13 g, 1.3 eq), DPPA (0.71 g, 4 eq) in 6 mL THF at 70° C. for 2 h. After removal of solvent, extraction with EtOAc and washing with saturated NaHCO$_3$, flash chromatography (5:1:95 MeOH:NH$_3$:DCM) provided 0.29 g of the desired azide (84% yield).

$^1$H NMR (CDCl$_3$ δ): 1.01 (m, 1 H) 1.20 (m, 2 H) 1.60 (m, 1 H) 1.80-2.10 (m, 8 H) 2.60-2.70 (m, 6 H) 2.82 (m, 1 H) 3.30-3.50 (m, 2 H) 4.50 (s, 2 H) 5.01 (m, 1 H) 7.00 (m, 1 H) 7.40 (m, 2 H) 7.58 (m, 1 H) 11.1 (s, 1 H, N—H)

$^{13}$C NMR (CDCl$_3$ δ): 16.0 23.5 23.7 30.4 31.5 42.9 51.9 53.9 55.0 55.2 59.8 117.3 117.4 120.2 124.3 130.2 137.8 139.0 146.0 158.1 162.4 177.0 HRMS for (MH+) $C_{24}H_{27}F_4N_7OS$: calcd: 538.2012; found: 538.2019.

The above azide (96 mg, 0.18 mmol, 1 eq) was dissolved in 3 mL ethyl ether and 0.2 mL LiAlH$_4$ (1 M in THF, 1.2 eq) was added and heated to 38° C. for 2 h. After removal of solvent, extraction with EtOAc and washing with saturated NaHCO$_3$, preparative TLC (5:1:95 MeOH:NH$_3$:DCM) provided 30 mg of the desired final product 1.

$^1$H NMR (CDCl$_3$ δ): 1.00 (m, 1 H) 1.20 (m, 2 H) 1.50-1.75 (m, 5 H) 1.80-1.95 (m, 4 H) 2.08 (m, 2 H) 2.60-2.80 (m, 4 H) 2.90 (m, 1 H) 3.20-3.50 (m, 2 H) 4.00 (s, 2 H) 5.00 (m, 1H) 7.00 (m, 1H) 7.30 (s, 1H) 7.38 (m, 1H) 7.58 (m, 1H) 11.2 (s, 1 H, N—H)

$^{13}$C NMR (CDCl$_3$ δ): 15.8 23.6 23.8 24.2 30.1 31.5 42.8 44.8 55.2 59.7 62.3 117.4 117.6 122.2 124.1 124.3 137.0 138.4 148.2 154.6 157.8 172.0 HRMS for (MH+) $C_{24}H_{30}F_4N_5O_2S$: calcd: 512.2107; found: 512.2111.

For the Synthesis of the Cross-Conjugated Compound:

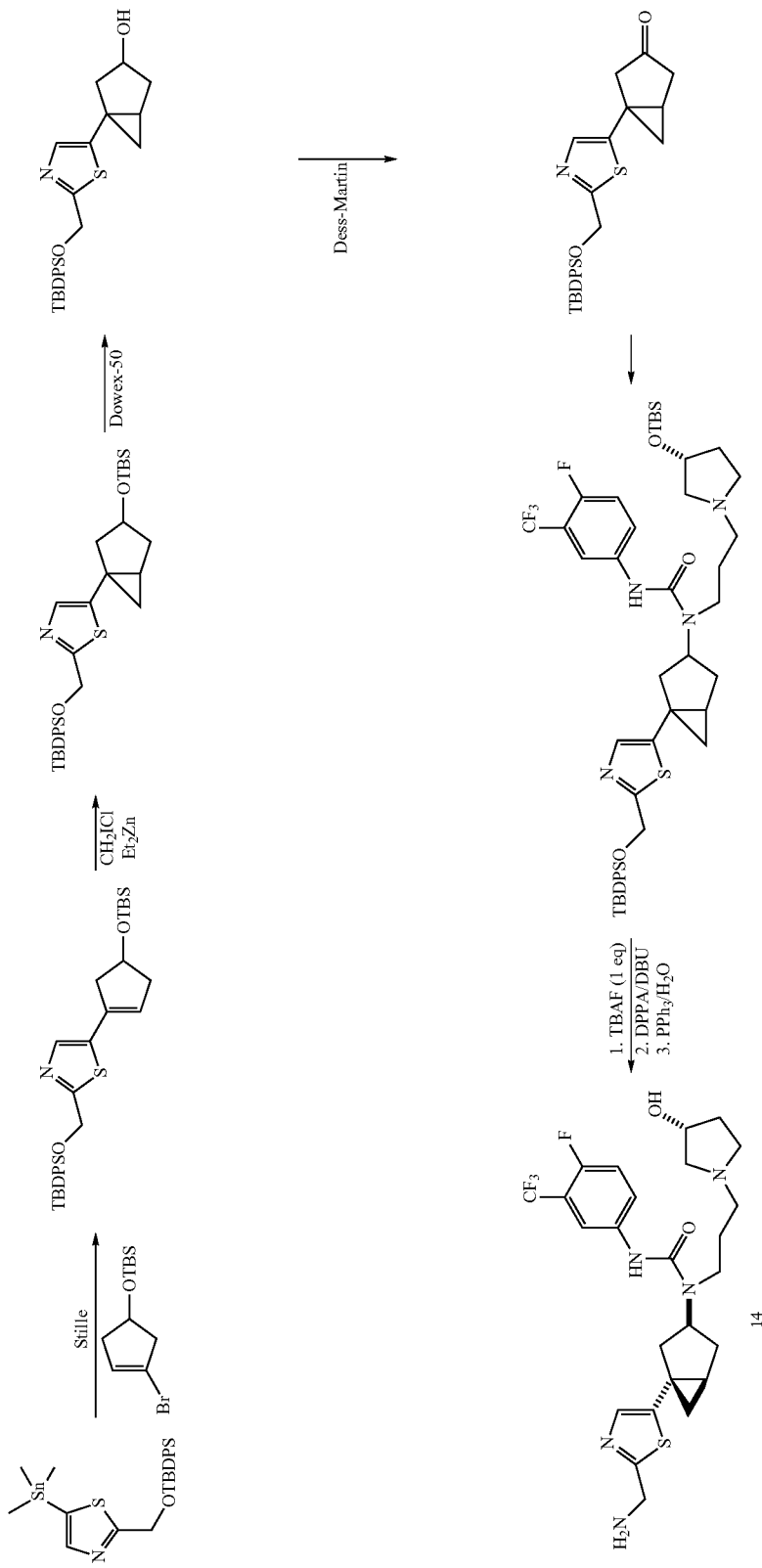

Synthesis of [3,1,0]bicyclohexyl Analogs (Cross Conjugated, Method 1)

Cyclopropanation reaction: To a solution of diethyl zinc (1 M solution in Hexanes, 1 mL, 5.5 eq.) in dichloroethane (10 mL) was added chloroiodomethane (0.1 mL, 7.5 eq.) drop wise at 0° C. The solution was stirred at that temperature for 10 minutes. A solution of olefin compound (0.1 g, 0.181 mmol) in dichloroethane (5mL) was added drop wise at 0° C. and stirred for 3 hours. The reaction was quenched by the addition of NH$_4$Cl solution and extracted with ethyl acetate. The solvent was removed in vacuo and the product was isolated by preparative TLC using 5% ethyl acetate in hexane to afford 0.055 g (54%) of cyclopropanated compound as oil.

$^1$H NMR (CDCl$_3$ δ): 0.072 (s, 6H), 0.909 (s, 9H), 1.0-1.06 (m, 3H), 1.61-2.18 (m, 4H), 4.35 (m, 1H), 4.92 (s, 2H), 7.34 (s, 1H), 7.40 (m, 5H), 7.71 (m, 5H). MS for (MH$^+$) C$_{32}$H$_{46}$NO$_2$SSi$_2^+$: calcd: 564.28; found: 564.17

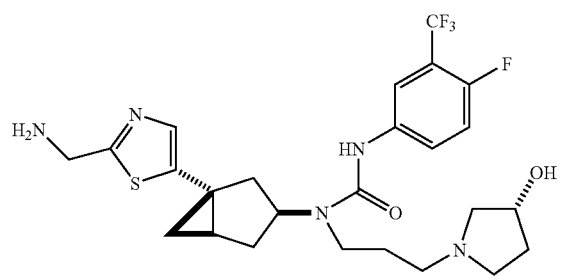

MOLECULAR STRUCTURE

Data for Compound 14:

$^1$H NMR (CDCl$_3$d): 1.01 (s, 1H), 1.24 (m, 2H), 1.50 (s, 1H), 1.65-1.75 (m, 3H), 1.94 (m, 2H), 1.97-2.27 (m, 3H), 2.41-2.66 (m, 3H), 3.11-3.44 (m, 9H), 4.23 (m, 1H), 4.85 (s, 1H), 7.24 (m, 2H), 7.65 (m, 1H), 7.77 (m, 1H), 8.50 (br s, 1H).

MS for (MH$^+$) C$_{25}$H$_{32}$F$_4$N$_5$O$_2$S$^+$: calcd: 542.22; found: 542.30.

For the Synthesis of Cyclohexenyl Analogs (Method 2):

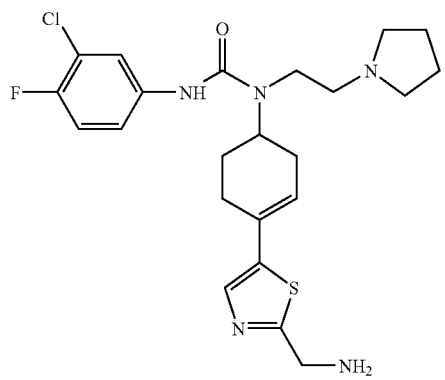

2

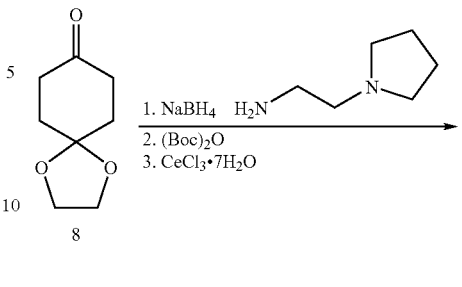

8

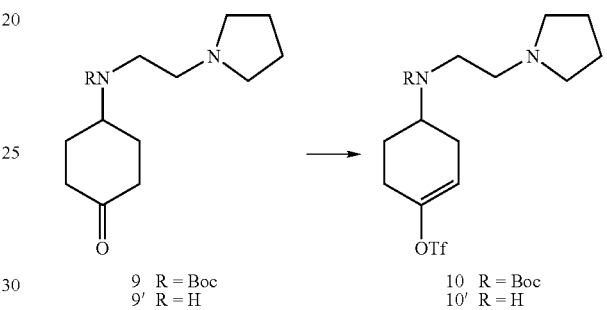

9  R = Boc
9' R = H

10  R = Boc
10' R = H

Ketone 8 (9.9 g, 63.5 mmol, 1 eq)/200 mL DCM/N-(2-aminoethyl)pyrrolidine (8.7 g, 1.2 eq)/Ti(OiPr)$_4$ (21.6 g, 1.2 eq) was stirred at room temperature for overnight. The mixture was cooled to 0° C. followed by addition of NaBH$_4$ (3.4 g, 1.4 eq). After another overnight stirring, 5 mL of MeOH was added. After 2 h, saturated Na$_2$CO$_3$ was added followed by extraction with EtOAc. Flash chromatography (10:1:90 MeOH:NH$_3$:DCM) provided 9.8 g of the desired product (60% yield).

$^1$H NMR (CDCl$_3$ δ): 1.30-1.40 (m, 2 H) 1.41-1.55 (m, 2 H) 1.65 (br s, 6 H) 1.80 (m, 2 H) 2.40 (m, 5 H) 2.52 (t, 3 H, J=7.1 Hz) 2.62 (t, 3 H, J=7.1 Hz) 3.80 (s, 4 H) MS: C$_{14}$H$_{27}$N$_2$O$_2$: 255 (MH)$^+$

This material (3.1 g, 12.2 mmol, 1 eq) was treated with Boc$_2$O (3.2 g, 1.2 eq), NaHCO$_3$ (2 g, 1.5 eq) in 40 mL THF and 40 mL water. The mixture was heated to 55° C. for 48 h. After cooling, extraction with EtOAc and drying the organic layer with Na$_2$CO$_3$, evaporation of the solvent afforded colorless syrup (4.4 g). This syrup was treated with CeCl$_3$.7H$_2$O (9 g, 2 eq), NaI (0.54 g, 0.3 eq) in 80 mL of CH$_3$CN at 80° C. nitrogen for 2 h. Another 4.5 g of CeCl$_3$.7H$_2$O (1 eq), NaI (0.54 g, 0.3 eq) and 60 mL of CH$_3$CN were added and the mixture was heated for 16 h. After cooling to room temperature, extraction with EtOAc, drying with Na$_2$SO$_4$, evaporation of solvent provided light yellow syrup 9 and 9' (3.1 g total, 9:9'=1.4:1).

The above material (3.1 g, 10 mmol) was dissolved in 1:1 Toluene/THF 50 mL, cooled to −78° C. followed by addition of 5.36 g of (Tf)$_2$NPh (15 mmol, 1.5 eq) and slow addition of KHMDS solution 30 mL (0.5 N in Toluene, 1.5 eq). After 4 hours of stirring, 40 mL of water was added into reaction mixture. This reaction mixture was slowly warmed up to room temperature followed by extraction of EtOAc. Flash chromatography (3:1:100 MeOH:NH₃:DCM) gave the first fraction as colorless syrup 10 (1.5 g)

1H NMR (CDCl₃ δ): 1.38 (s, 9 H) 1.69 (m, 4 H) 1.80 (m, 1 H) 1.88 (m, 1 H) 2.20 (m, 1 H) 2.26-2.30 (m, 2 H) 2.47 (m, 7 H) 3.13 (br s, 2 H) 4.03 (br s, 1 H) 5.62 (m, 1 H) Chromatography also gave the second fraction as colorless syrup 10' (1.1 g) 1H NMR (CDCl₃ δ): 1.53 (m, 1 H) 1.67 (m, 4 H) 1.89-1.92 (m, 3 H) 2.31 (m, 2 H) 2.42 (m, 5 H) 2.52 (t, 2 H, J=6 Hz) 2.67 (m, 3 H) 5.59 (m, 1 H)

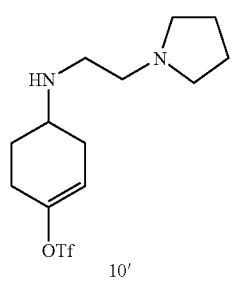

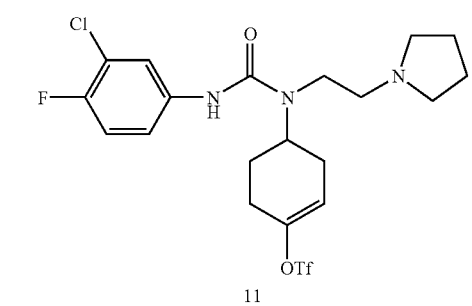

This material 10' (1 g, 2.9 mmol, 1 eq)/15 mL DCM/4-fluro-3-chlorophenyl isocyanate (0.6 g, 3.5 mmol, 1.2 eq) stirred at room temperature under N₂ for 3 hours. Saturated NaCl solution was added followed by extraction with EtOAc. Flash chromatography (40:100 EtOAc/hexane) gave 11 as white solid (1.48 g, 96% yield).

¹H NMR (CDCl₃ δ): 1.86 (m, 6 H) 2.19 (m, 1H) 2.32-2.36 (m, 2 H) 2.56 (m, 1 H) 2.67-2.72 (m, 6 H) 3.23 (m, 2 H) 4.36 (m, 1 H) 5.69 (m, 1 H) 6.96 (t, 1 H, J=8.8 Hz) 7.08 (m, 1 H) 7.40 (m, 2 H) 11.07 (m, 1 H)

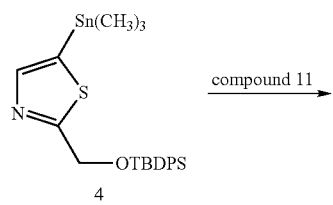

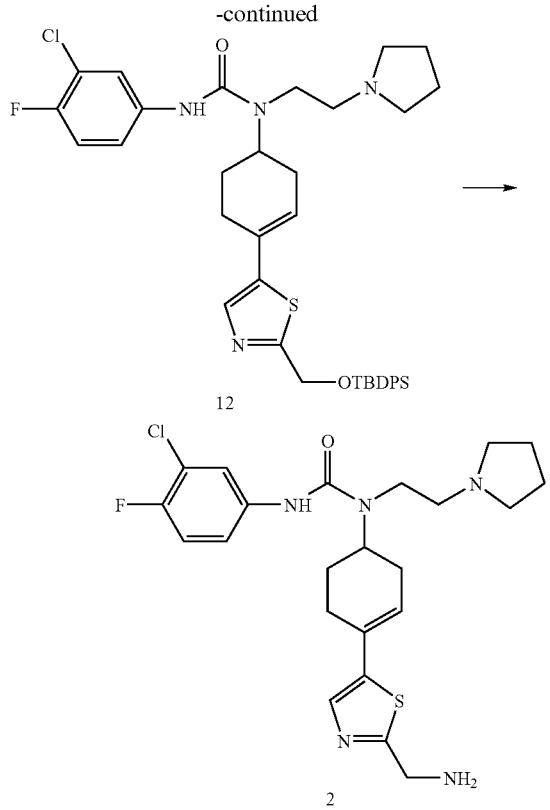

The conversion of 5 to 12 and then to 2 followed method 1 as described above. Compound 2:

¹H NMR (CDCl₃ δ): 1.60-1.95 (m, 9H) 2.19 (m, 1H) 2.32 (m, 1 H) 2.56 (m, 2 H) 2.60-2.80 (m, 6H) 3.20 (br s, 2H) 4.06 (br s, 1H) 4.40 (m, 1H) 5.90 (br s, 1H) 6.96 (t, 1H, J=8.8 Hz) 7.08 (m, 1 H) 7.40 (m, 2 H) 11.00 (br s, 1 H) LC/MS: t=4.19 min. MS: C₂₃H₃₀ClFN₅OS: 479 (MH)⁺.

Further, by modifying the above schemes and experimental examples, the following compounds can be prepared.

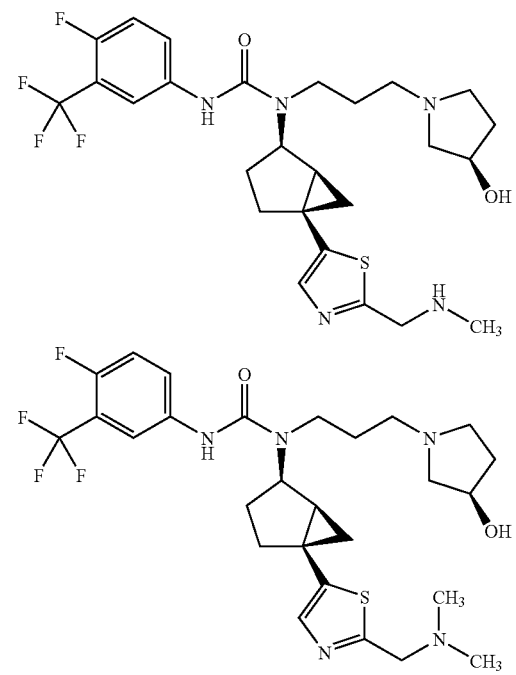

-continued

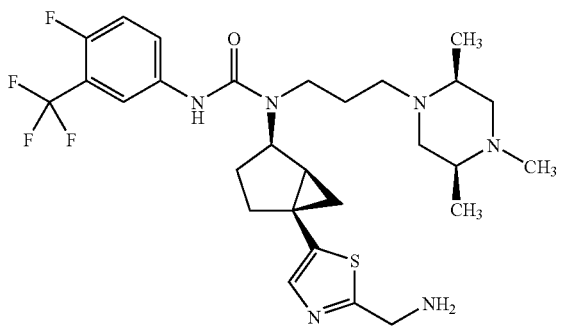

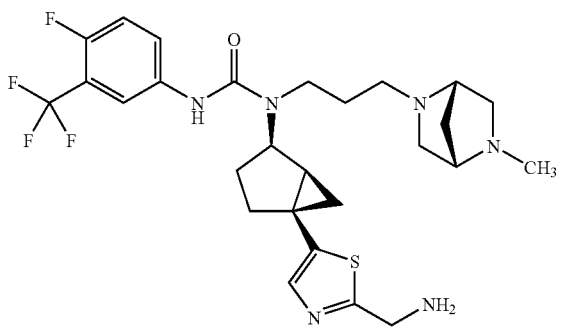

and

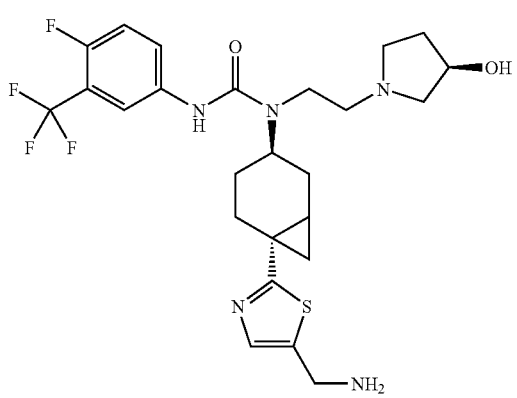

-continued

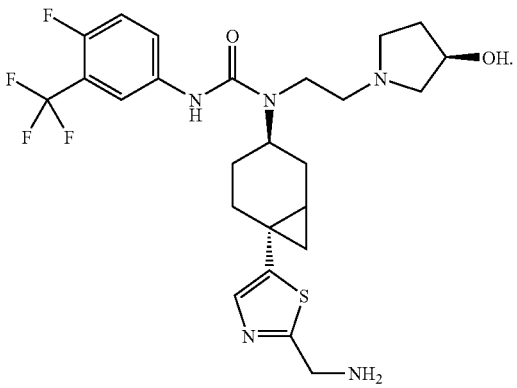

Herg-Rb Two Phase Screen

Herg-Rb data (μg/mL) (%) was determined by the following two phase screen. The first phase is a cell-handling phase in which cells are loaded with rubidium, drugs are added and efflux initiated by KCl-depolarization. The second phase is measurement of rubidium content in cell supernatants that are collected at the end of the cell-handling phase. CHO cells expressing hERG in a stable manner are used for these studies. Cells are plated into 96-well dishes one day prior to study. After overnight culture, the normal tissue culture medium is removed and cells are loaded with rubidium for 3 hours in a HEPES-buffered physiological saline solution containing 5 mM rubidium chloride in place of potassium chloride. During the final 30 minutes of rubidium loading cells are pre-equilibrated with test articles at 1.5 μg/ml and 5 μg/ml. Cells are then washed with rubidium-free HEPES buffered physiological saline solution containing 5 mM KCl to remove all extracellular rubidium. The final step of the cell handling phase is to depolarize the cells in HEPES buffered physiological saline containing 50 mM KCl. This opens hERG channels and permits efflux of rubidium. Supernatants are collected after 5 minutes and rubidium content is measured using a flame atomic absorbance spectrometer with a robot for sampling from 96-well plates (ICR-8000, Aurora Biomed Inc., Vancouver, British Columbia). In cases where the channel is blocked the amount of rubidium efflux is reduced. Drug effects are calculated based on the difference between wells with no added compound and wells in which there is complete block of hERG channels with a well-known positive standard (10 μM dofetilide).

| EX. | MOL STRUCTURE | herg-Rb 5 µg/mL (%) | herg-Rb 1.5 µg/mL (%) |
|---|---|---|---|
| 1 | [structure: 3-chloro-4-fluorophenyl urea with pyrrolidinylethyl, cyclohexenyl-thiophene-CH2NH2] | 26 | 22 |
| 2 | [structure: 3-chloro-4-fluorophenyl urea with pyrrolidinylethyl, cyclohexenyl-thiophene-CH2N(CH3)2] | N/A | N/A |
| 3 | [structure: 3-chloro-4-fluorophenyl urea with pyrrolidinylethyl, cyclohexenyl-thiophene-CH2-azetidinyl] | 15 | −1 |

-continued

| EX. | MOL STRUCTURE | herg-Rb 5 µg/mL (%) | herg-Rb 1.5 µg/mL (%) |
|---|---|---|---|
| 4 | | 20 | −1 |
| 5 | | 6 | 0 |
| 6 | | N/A | N/A |

-continued
| EX. | MOL STRUCTURE | herg-Rb 5 μg/mL (%) | herg-Rb 1.5 μg/mL (%) |
|---|---|---|---|
| 7 | 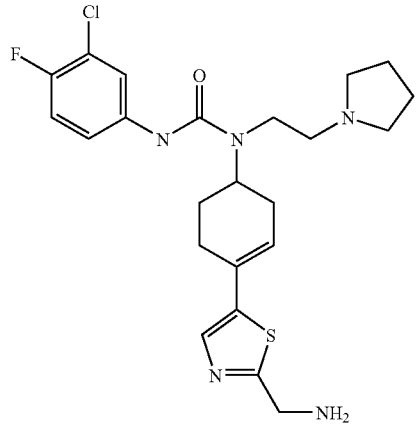 | 10 | −1 |
| 8 | 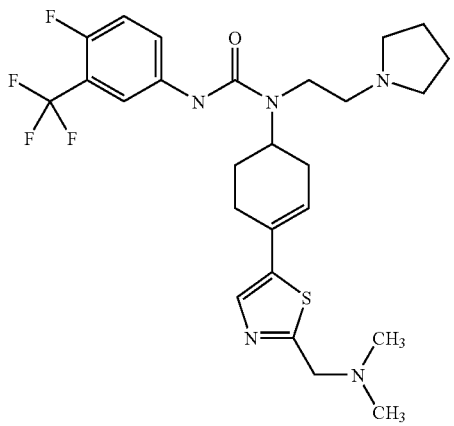 | N/A | N/A |
| 9 | 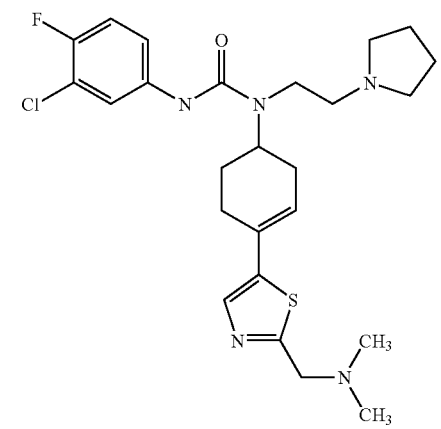 | N/A | N/A |

-continued
| EX. | MOL STRUCTURE | herg-Rb 5 μg/mL (%) | herg-Rb 1.5 μg/mL (%) |
|---|---|---|---|
| 10 | 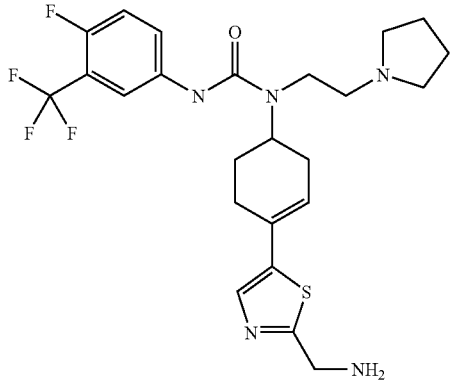 | 26 | 9 |
| 11 | 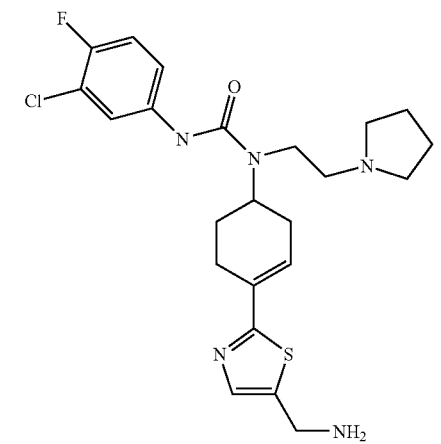 | 14 | 9 |
| 12 | 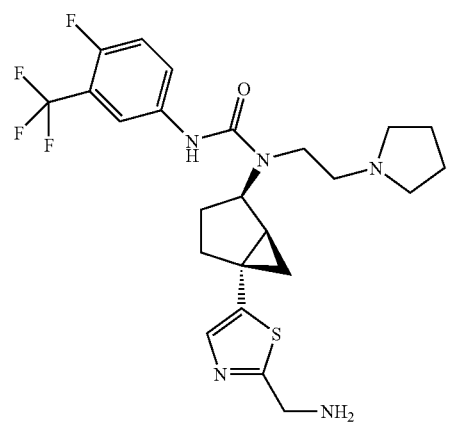 | 16 | 13 |

-continued

| EX. | MOL STRUCTURE | herg-Rb 5 μg/mL (%) | herg-Rb 1.5 μg/mL (%) |
|---|---|---|---|
| 13 | | 8 | 13 |
| 14 | | N/A | N/A |
| 15 | | −4 | −4 |
| 16 | | −8 | −11 |

| EX. | MOL STRUCTURE | herg-Rb 5 µg/mL (%) | herg-Rb 1.5 µg/mL (%) |
|---|---|---|---|
| 17 | | 14 | 0 |
| 18 | | −4 | −5 |
| 19 | | 3 | −10 |

-continued

| EX. | MOL STRUCTURE | herg-Rb 5 µg/mL (%) | herg-Rb 1.5 µg/mL (%) |
|---|---|---|---|
| 20 | 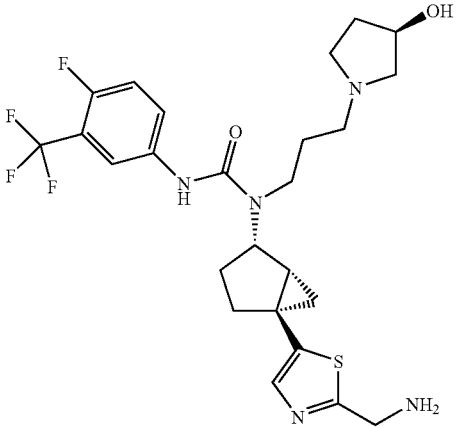 chiral | N/A | N/A |
| 21 | 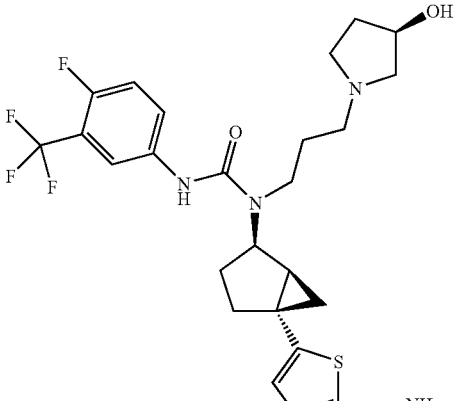 chiral | N/A | N/A |

MCH Receptor Binding Assay:

Membranes from CHO cells expressing the MCH receptor were prepared by lysing cells with 5 mM HEPES for 15 min at 4 C. Cell lysates were centrifuged (12.5000×g, 15 min) and the pellet was re-suspended in 5 mM HEPES. For each 96-well plate (Microlite, Dynex Technologies), 1 mg of cell membranes were incubated with 10 mg of wheat germ agglutinin SPA beads (Amersham) for 5 min at 4 C in a volume of 10 ml of binding buffer (25 mM HEPES, 10 mM $MGCl_2$, 10 mM NaCl, 5 mM $MnCl_2$, 0.1% BSA). The membrane/bead mixture was centrifuged (1500×g, 3.5 min), the supernatant was aspirated, and the pellet was resuspended in 10 ml binding buffer. The centrifugation, aspiration and resuspension were then repeated. The membrane/bead mixture (100 µl) was then added to 96-well plates containing 50 µl of 500 pM [$^{125}$I]-MCH (NEN) and 50 ml of the appropriate concentration of compound (4× the desired final concentration). Nonspecific binding was determined by including 1 µM MCH in the binding reaction. The binding reaction was incubated at room temperature for 2 h. Plates were then analyzed in a TOPCOUNT microplate scintillation counter (Packard). Data was analyzed and Ki values were determined using GraphPad Prism.

Compounds with Ki values greater than 100 nM are designated in the table below as C class compounds.

Compounds with Ki values between 30 and 100 nM are designated in the table below as B class compounds.

Compounds with Ki values less than 30 nM are designated in the table below as A class compounds.

In a preferred embodiment of the invention, Example 1, a Ki value of 8 nM was observed.

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

| EX. | MOLECULAR STRUCTURE | Class |
|---|---|---|
| 1 | *[structure: 1-(3-chloro-4-fluorophenyl)-3-(2-(pyrrolidin-1-yl)ethyl)-3-(4-(5-(aminomethyl)thiophen-2-yl)cyclohex-3-en-1-yl)urea]* | A |
| 2 | *[structure: 1-(3-chloro-4-fluorophenyl)-3-(2-(pyrrolidin-1-yl)ethyl)-3-(4-(5-((dimethylamino)methyl)thiophen-2-yl)cyclohex-3-en-1-yl)urea]* | C |
| 3 | *[structure: 1-(3-chloro-4-fluorophenyl)-3-(2-(pyrrolidin-1-yl)ethyl)-3-(4-(5-(azetidin-1-ylmethyl)thiophen-2-yl)cyclohex-3-en-1-yl)urea]* | C |

-continued
| EX. | MOLECULAR STRUCTURE | Class |
|---|---|---|
| 4 | 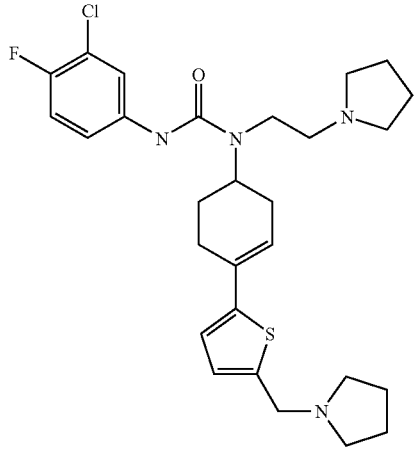 | C |
| 5 | 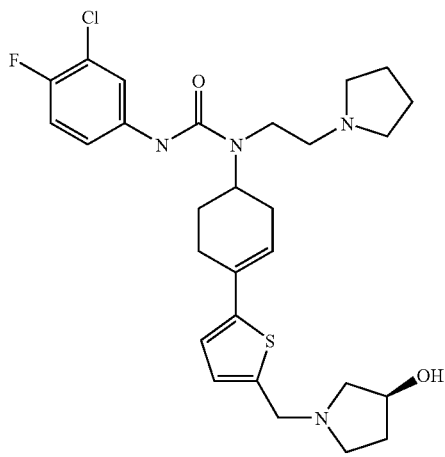 | B |
| 6 | 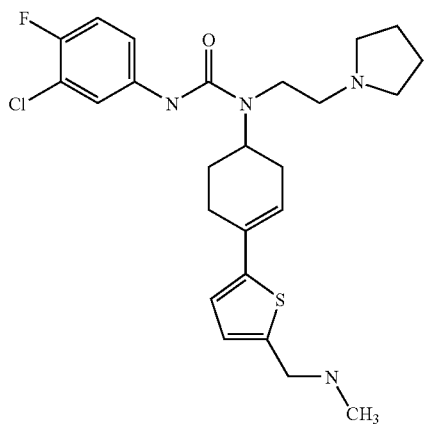 | A |

-continued
| EX. | MOLECULAR STRUCTURE | Class |
|---|---|---|
| 7 | 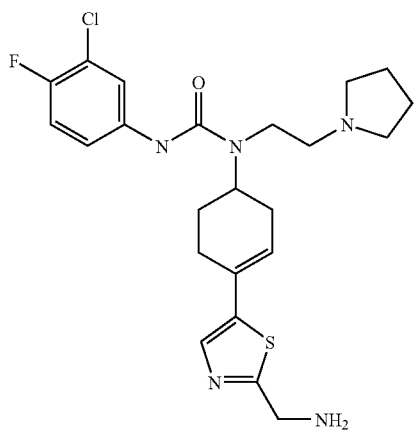 | A |
| 8 | 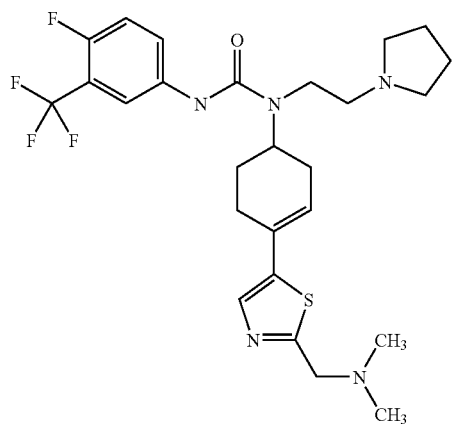 | C |
| 9 | 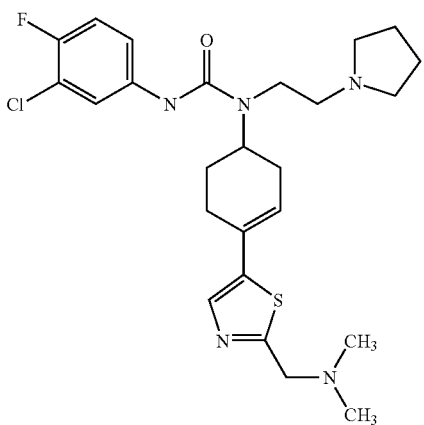 | C |

-continued
| EX. | MOLECULAR STRUCTURE | Class |
|---|---|---|
| 10 | 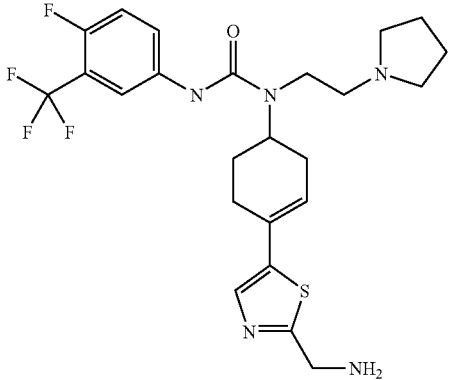 | A |
| 11 | 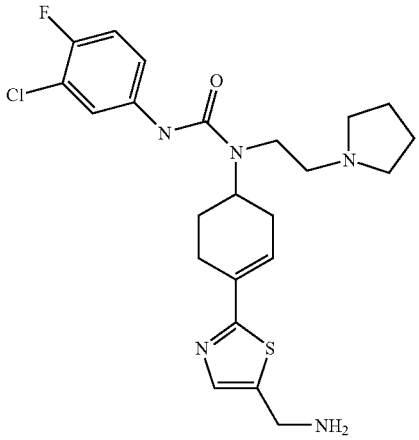 | A |
| 12 | 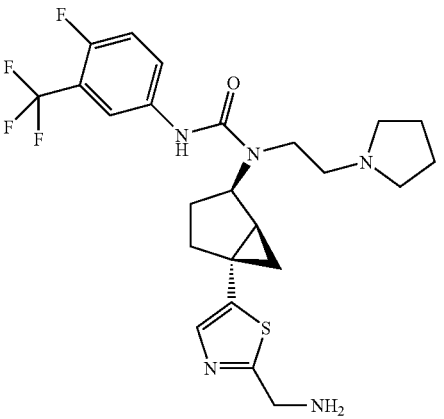 | C |

-continued

| EX. | MOLECULAR STRUCTURE | Class |
|---|---|---|
| 13 | 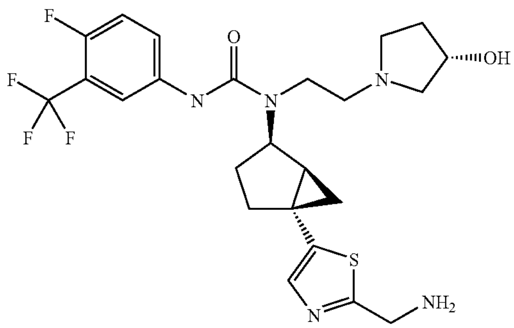 | B |
| 14 | 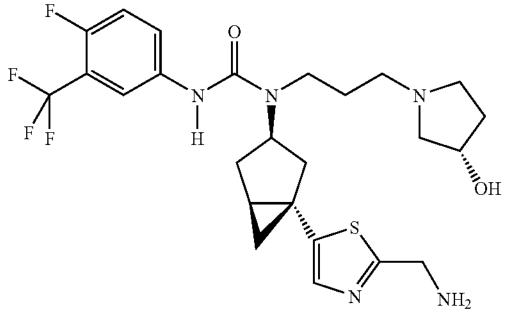 | C |
| 15 | 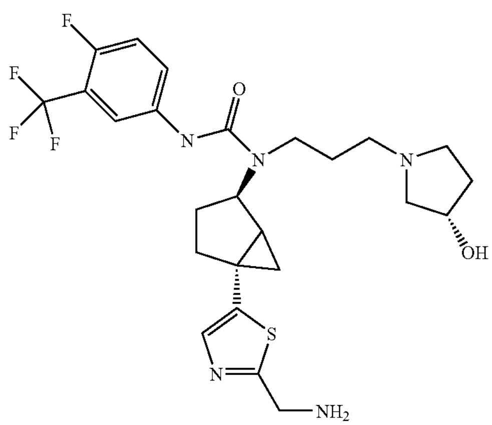 | B |
| 16 | 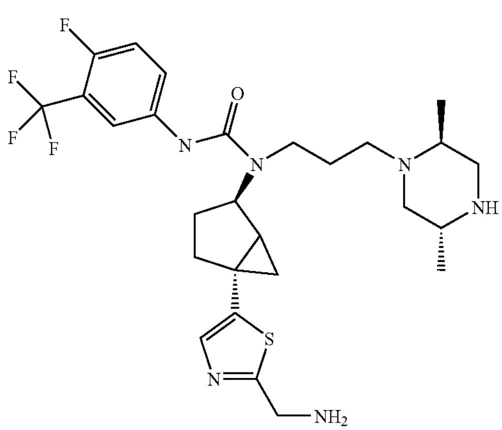 | A |

-continued
| EX. | MOLECULAR STRUCTURE | Class |
|-----|---------------------|-------|
| 17  | 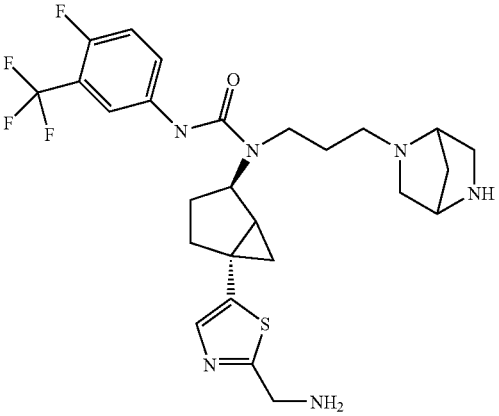 | B |
| 18  | 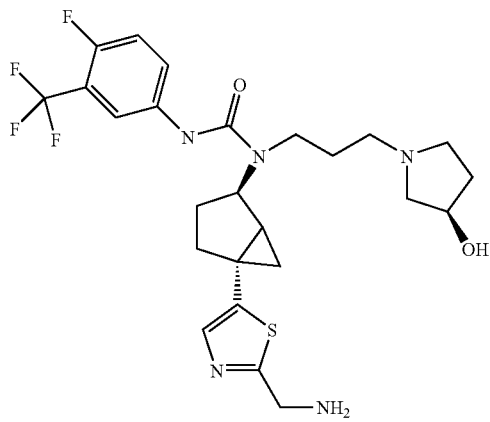 | A |
| 19  | 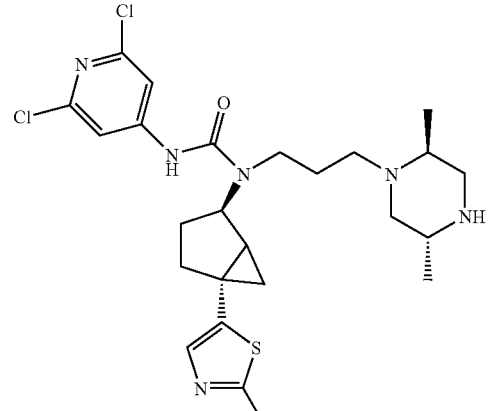 | A |

| EX. | MOLECULAR STRUCTURE | Class |
|---|---|---|
| 20 | 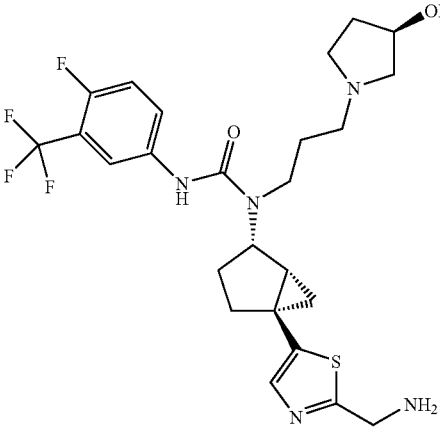 chiral | C |
| 21 | 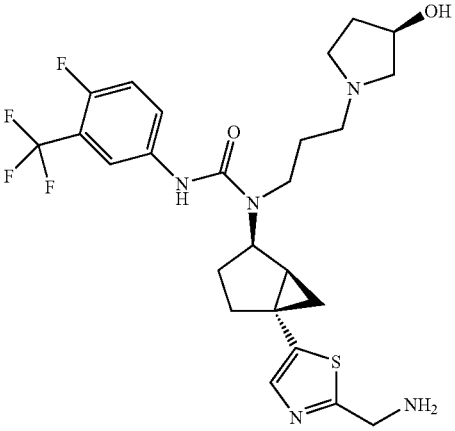 chiral | A |

What is claimed is:

1. A compound represented by the structural formula

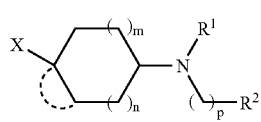

formula I or a pharmaceutically acceptable salt thereof, wherein

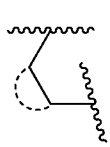

represents either (a) a single bond (b) a double bond, or (c) a cycloalkyl ring where the dashed line is $-(CR^{14}R^{15})_s-$ where s is 1, 2, 3 or 4;

m is 0, 1 or 2;
n is 0 or 1, where the sum of n and m is 1 to 3;
p is 0, 1, 2, 3 or 4;
X is selected from the group consisting of:

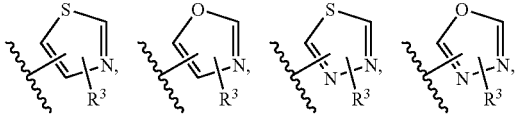

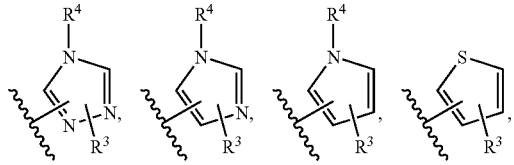

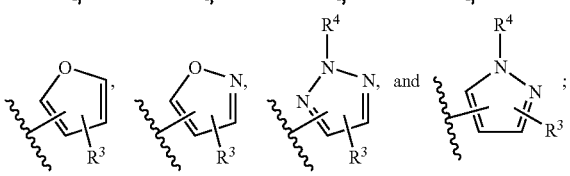

$R^1$ is

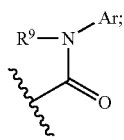

$R^2$ is

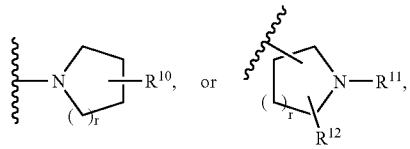

where r is 0 or 1;
$R^3$ is —$(CR^5R^6)_{1-3}$—$NR^7R^8$, or $R^3$ is

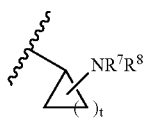

where t is 1, 2, 3, 4 or 5;
$R^4$ is hydrogen or alkyl;
$R^5$ and $R^6$ can be the same or different, each being hydrogen or alkyl;
$R^7$ is hydrogen, alkyl, acyl, alkoxycarbonyl, arylsulfonyl or alkylsulfonyl;
$R^8$ is hydrogen, alkyl, acyl, —C(O)NH$_2$, —C(O)NH-alkyl, —C(O)N(alkyl)$_2$, alkoxycarbonyl, arylsulfonyl or alkylsulfonyl;
$R^9$ is hydrogen or alkyl;
$R^{10}$ is 1 to 3 moieties, each $R^{10}$ is independently selected from the group consisting of hydrogen, hydroxy, alkoxy, alkoxyalkyl, hydroxyalkyl, alkyl and halo, with the proviso that $R^{10}$ cannot be halo when it is attached to the carbon adjacent to N;
$R^{11}$ is hydrogen, alkyl, alkoxyalkyl, hydroxyalkyl, acyl, alkoxycarbonyl, —C(O)NR$^7$R$^8$, alkylC(O)NR$^7$R$^8$, arylsulfonyl, alkylsulfonyl or -alkylC(O)$_2$R$^4$;
$R^{12}$ is 1 to 4 moieties, each $R^{12}$ is independently selected from the group consisting of hydrogen, alkyl, alkoxyalkyl or hydroxyalkyl;
Ar is $(R^{13})_u$-substituted aryl, where u is a number from 1 to 3; and each $R^{13}$ is independently selected from the group consisting of hydrogen, hydroxy, halo, alkyl, alkoxy, —OCF$_3$, —CF$_3$, —SO$_2$-alkyl, —NO$_2$, —SCF$_3$ and —CN, or two $R^{13}$ moieties on adjacent carbons of the aryl or heteroaryl ring can be linked to form

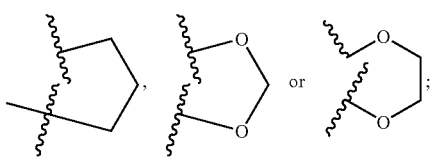

$R^{14}$ is hydrogen, alkyl, —CH$_2$OH, halo, —CN, —OH, alkoxy or —NR$^7$R$^8$; and
$R^{15}$ is hydrogen, alkyl, —CH$_2$OH, halo, —CN, —OH, alkoxy or —NR$^7$R$^8$.

2. The compound of claim 1 wherein

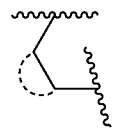

represents either (a) a double bond or (b)

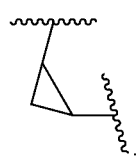

3. The compound of claim 1 wherein m is 0 or 1, n is 0 or 1 and p is 2 or 3.

4. The compound of claim 1 wherein X is selected from the group consisting of:

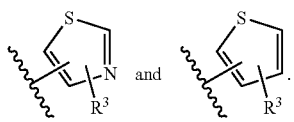

5. The compound of claim 1 wherein $R^1$ is

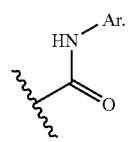

6. The compound of claim 1 wherein $R^2$ is

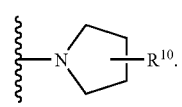

7. The compound of claim 1 wherein $R^3$ is —CH$_2$—NR$^7$R$^8$.

8. The compound of claim 1 wherein $R^7$ is hydrogen or alkyl and $R^8$ is hydrogen or alkyl.

9. The compound of claim 1 wherein $R^{10}$ is 1 or 2 moieties and each $R^{10}$ is independently selected from the group consisting of hydrogen, hydroxy and alkoxy.

10. The compound of claim 1 wherein $R^{10}$ is 1 moiety and $R^{10}$ is independently selected from the group consisting of hydrogen and hydroxy.

11. The compound of claim 1 wherein $R^{11}$ is hydrogen or alkyl.

12. The compound of claim 1 wherein $R^{12}$ is 1 or 2 moieties, where each $R^{12}$ moiety is independently selected from the group consisting of hydrogen, alkyl, hydroxyalkyl and alkoxyalkyl.

13. The compound of claim 1 wherein Ar is $(R^{13})_2$-substituted aryl, wherein each $R^{13}$ is independently selected from the group consisting of halo and —$CF_3$.

14. The compound of claim 1 wherein $R^{14}$ is hydrogen or alkyl and $R^{15}$ is hydrogen or alkyl.

15. The compound of claim 1 wherein

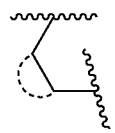

represents either (a) a double bond or (b) —$C(R^{14}R^{15})$—;
m is 1 or 2;
n is 0 or 1;
p is 2 or 3;
X is selected from the group consisting of

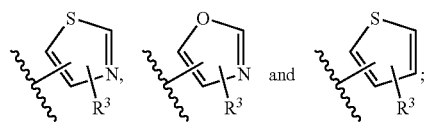

$R^1$ is

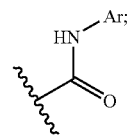

$R^2$ is

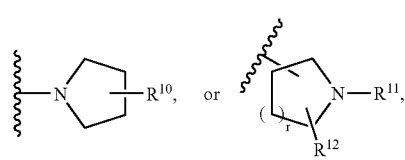

where r is 0, or 1;
$R^3$ is —$C(R^5R^6)$—$NR^7R^8$;
$R^7$ is hydrogen or alkyl;
$R^8$ is hydrogen or alkyl;
$R^{10}$ is 1 or 2 moieties and each $R^{10}$ is independently selected from the group consisting of hydrogen, hydroxy and alkoxy;
$R^{11}$ is hydrogen or alkyl;
$R^{12}$ is selected from the group consisting of hydrogen, alkyl, hydroxyalkyl and alkoxyalkyl;

Ar is $(R^{13})_2$-substituted aryl, wherein each $R^{13}$ is independently selected from the group consisting of halo and —$CF_3$;
$R^{14}$ is hydrogen or alkyl; and
$R^{15}$ is hydrogen or alkyl.

16. The compound of claim 1

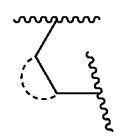

represents either (a) a double bond or (b) —$C(R^{14}R^{15})$—;
m is 1;
n is 0;
p is 2 or 3;
X is selected from the group consisting of

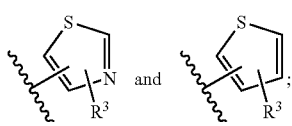

$R^1$ is

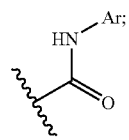

$R^2$ is

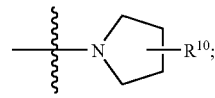

$R^3$ is —$C(R^5R^6)$—$NR^7R^8$;
$R^5$ and $R^6$ can be the same or different, each being hydrogen or alkyl;
$R^7$ is hydrogen or alkyl;
$R^8$ is hydrogen or alkyl;
$R^{10}$ is hydroxy;
$R^{11}$ is hydrogen or alkyl;
$R^{12}$ is 1 to 4 moieties, each $R^{12}$ is independently selected from the group consisting of hydrogen and alkyl;
Ar is $(R^{13})_u$-substituted phenyl, where u is 2; and each $R^{13}$ is independently selected from the group consisting of hydrogen, halo, —$OCF_3$, —$CF_3$ and —CN;
$R^{14}$ is hydrogen or alkyl; and
$R^{15}$ is hydrogen or alkyl.

17. A compound selected from the group consisting of
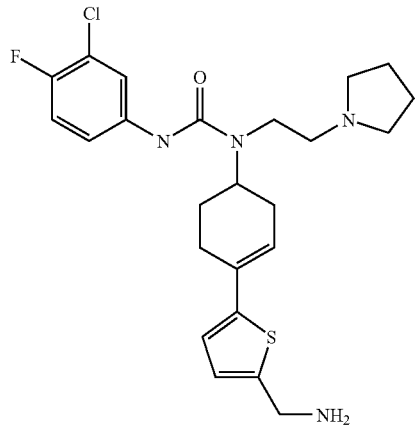
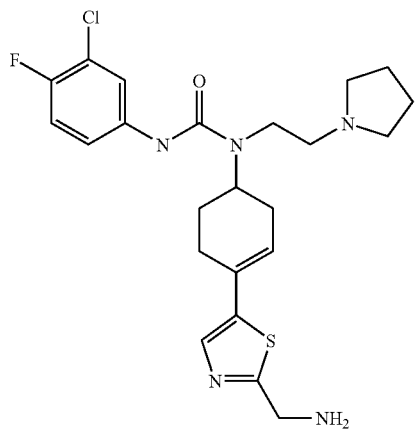
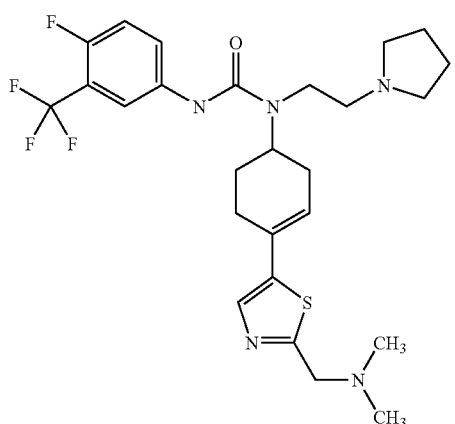
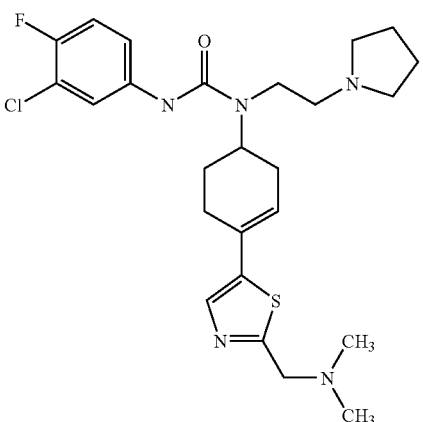
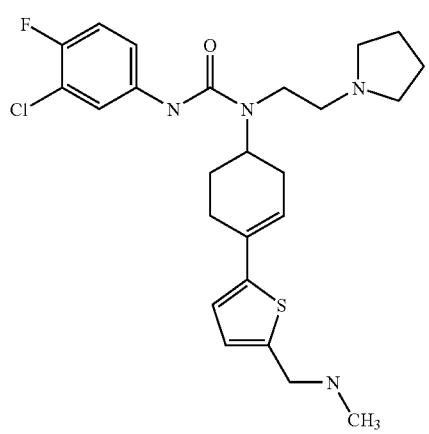
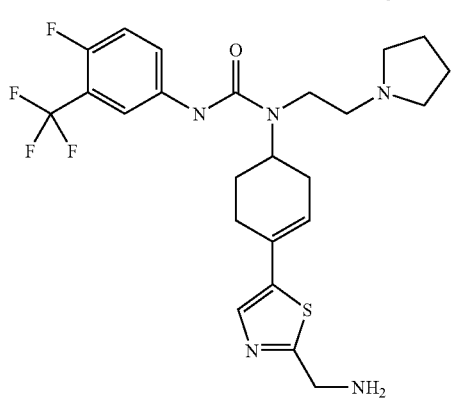

-continued
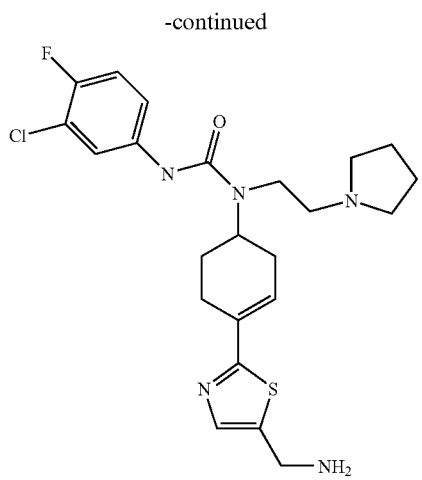
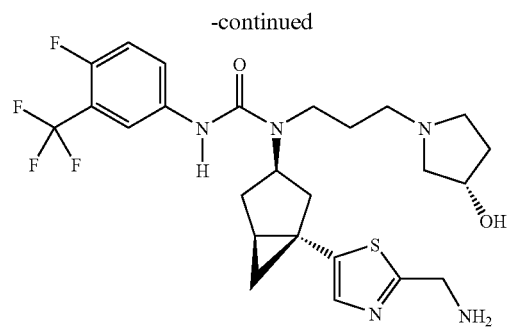
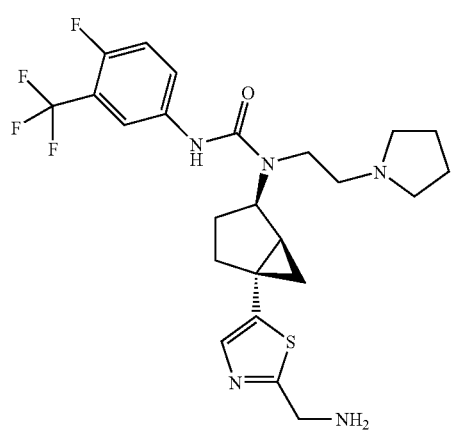
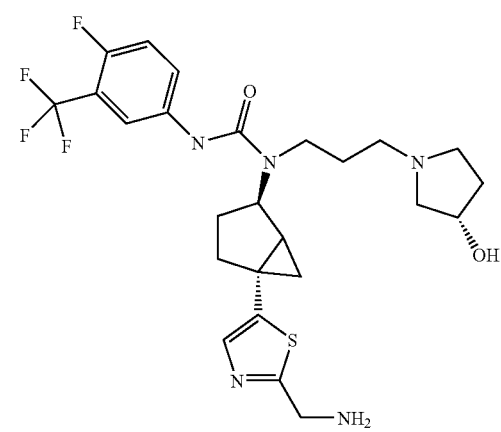
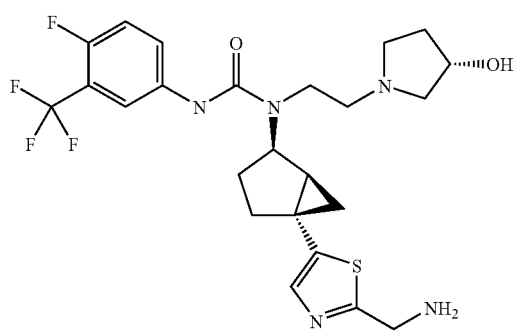
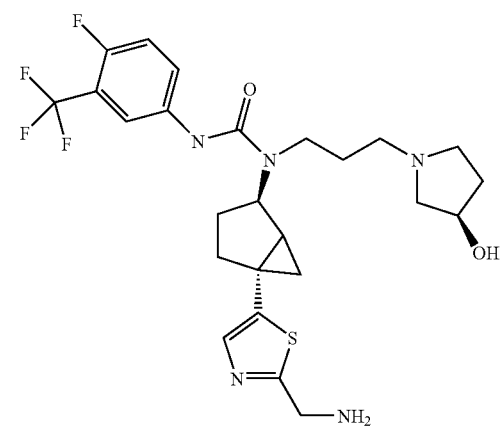

-continued

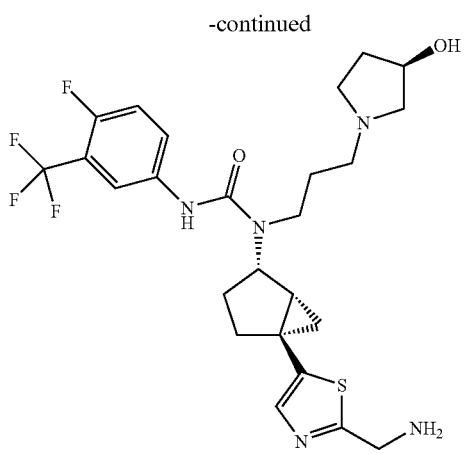

and

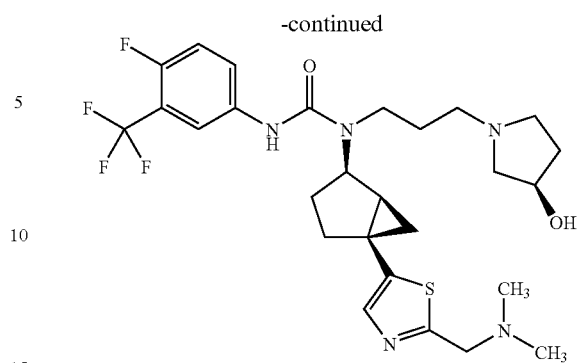

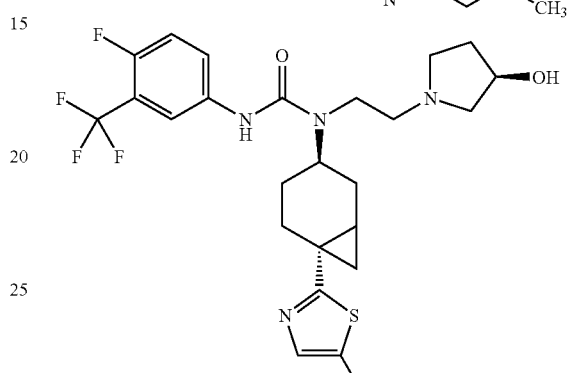

and

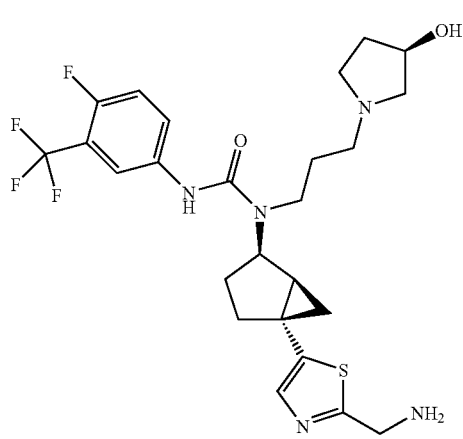

or a pharmaceutically acceptable salt thereof.

18. A compound selected from the group consisting of

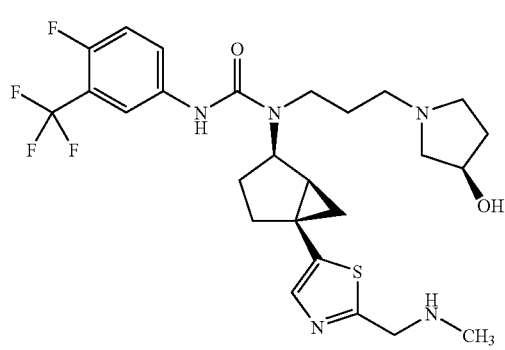

or a pharmaceutically acceptable salt thereof.

19. A pharmaceutical composition comprising a therapeutically effective amount of at least one compound of claim 1 in combination with at least one pharmaceutically acceptable carrier.

20. A pharmaceutical composition comprising a therapeutically effective amount of at least one compound of claim 17 in combination with at least one pharmaceutically acceptable carrier.

21. A pharmaceutical composition comprising a therapeutically effective amount of at least one compound of claim 18 in combination with at least one pharmaceutically acceptable carrier.

* * * * *